(12) United States Patent
Nakayama et al.

(10) Patent No.: US 11,009,414 B2
(45) Date of Patent: May 18, 2021

(54) SENSOR SYSTEM FOR CALCULATING PRESSING FORCE OR MOMENT BASED ON SIGNALS OUTPUT BY KINESTHETIC-SENSE SENSORS, ROBOT HAND INCLUDING THE SENSOR SYSTEM, AND METHOD FOR CALIBRATING THE SENSOR SYSTEM

(71) Applicant: Toyota Jidosha Kabushiki Kaisha, Toyota (JP)

(72) Inventors: Takahiro Nakayama, Nagoya (JP); Motohiro Fujiyoshi, Nagakute (JP); Yoshiyuki Hata, Nagakute (JP); Yoshiteru Omura, Nagakute (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 16/552,621

(22) Filed: Aug. 27, 2019

(65) Prior Publication Data
US 2020/0072691 A1 Mar. 5, 2020

(30) Foreign Application Priority Data
Aug. 30, 2018 (JP) .............................. JP2018-161365

(51) Int. Cl.
*G01L 5/16* (2020.01)
*G01L 5/161* (2020.01)
*A61B 5/103* (2006.01)

(52) U.S. Cl.
CPC ............ *G01L 5/161* (2013.01); *A61B 5/1036* (2013.01); *A61B 2562/0247* (2013.01)

(58) Field of Classification Search
CPC ......... G01L 5/161; G01L 5/162; G01L 5/009; G01L 5/226; G01L 5/228
See application file for complete search history.

(56) References Cited

U.S. PATENT DOCUMENTS

| 3,952,880 A | * | 4/1976 | Hill | ........................ | B25J 19/021 |
| | | | | | 414/5 |
| 6,886,415 B1 | * | 5/2005 | Kurogi | ................... | B25J 13/084 |
| | | | | | 73/862.045 |

(Continued)

FOREIGN PATENT DOCUMENTS

| CN | 106335053 A | 1/2017 |
| JP | 2008164556 A | 7/2008 |

(Continued)

*Primary Examiner* — Tran M. Tran
(74) *Attorney, Agent, or Firm* — Dinsmore & Shohl LLP

(57) ABSTRACT

A sensor system includes a substrate with a reference plane, a plurality of kinesthetic-sense sensors disposed on the substrate, each of the plurality of kinesthetic-sense sensors being configured to output signals of three axial directions corresponding to an orthogonal-axis direction orthogonal to the reference plane and two axial directions parallel to the reference plane, respectively, according to an external force from an object received at a force receiving part, a control unit configured to determine whether or not a value of each of the signals is larger than a predetermined threshold, and calculate a pressing force in the orthogonal-axis direction or a moment around the orthogonal axis received from the object based on a result of the determination, and an output unit configured to output a result of the calculation.

9 Claims, 21 Drawing Sheets

(56) References Cited

U.S. PATENT DOCUMENTS

| | | | | |
|---|---|---|---|---|
| 7,669,480 B2* | 3/2010 | Maekawa | ............... | B25J 13/082 |
| | | | | 73/777 |
| 8,096,173 B2* | 1/2012 | Isono | ................. | G01M 17/021 |
| | | | | 73/146 |
| 8,644,986 B2* | 2/2014 | Tsuboi | ................. | G05B 13/021 |
| | | | | 700/245 |
| 9,032,603 B2* | 5/2015 | Yamamoto | ............ | B23P 19/105 |
| | | | | 29/407.1 |
| 9,134,189 B2* | 9/2015 | Hata | ........................ | G01L 1/144 |
| 9,144,908 B2* | 9/2015 | Saen | ........................ | B25J 13/083 |
| 9,205,561 B2* | 12/2015 | Ikebe | ..................... | B25J 9/1694 |
| 9,215,089 B2* | 12/2015 | Muroyama | ............. | G01L 1/142 |
| 9,459,136 B2* | 10/2016 | Sato | ........................ | G01L 5/009 |
| 9,696,221 B2* | 7/2017 | Lauzier | ................. | B25J 9/0081 |
| 9,816,886 B2* | 11/2017 | Inazumi | ................. | G01L 5/167 |
| 9,851,266 B2* | 12/2017 | Nakamura | ............. | G01L 5/228 |
| 10,065,309 B2* | 9/2018 | Rose | .................... | B25J 15/0028 |
| 10,293,490 B2* | 5/2019 | Charalambides | ....... | G01L 1/205 |
| 10,442,091 B2* | 10/2019 | Kondoh | ................... | G01L 5/00 |
| 10,564,059 B2* | 2/2020 | Okada | .................... | G01L 5/165 |
| 2014/0109696 A1* | 4/2014 | Chen | ........................ | G01L 1/00 |
| | | | | 73/862.541 |
| 2018/0117772 A1* | 5/2018 | Ikebe | ................... | B25J 15/0028 |
| 2018/0169854 A1* | 6/2018 | Shiratsuchi | ............. | B25J 9/042 |

FOREIGN PATENT DOCUMENTS

| | | |
|---|---|---|
| JP | 2011158404 A | 8/2011 |
| TW | 201416652 A | 5/2014 |

* cited by examiner

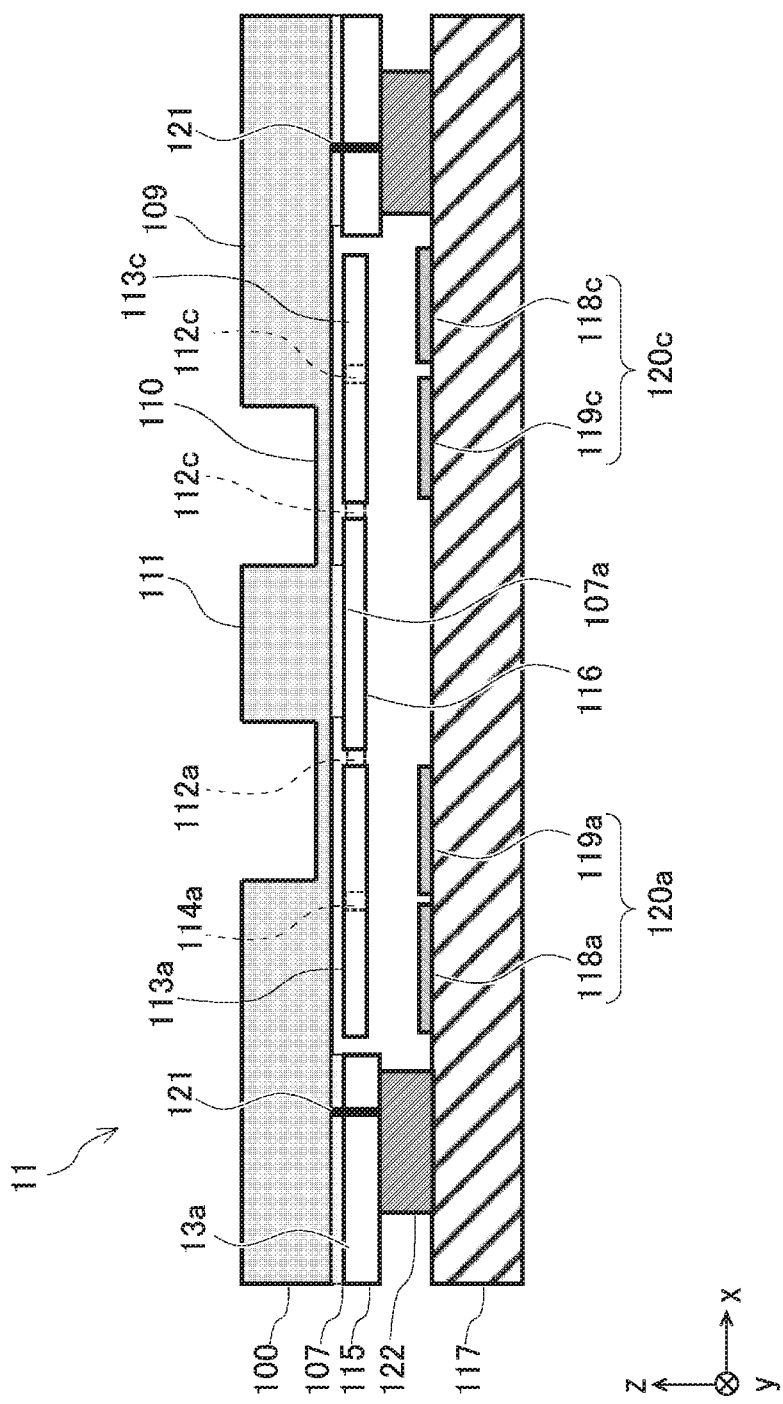

SENSOR SYSTEM FOR CALCULATING PRESSING FORCE OR MOMENT BASED ON SIGNALS OUTPUT BY KINESTHETIC-SENSE SENSORS, ROBOT HAND INCLUDING THE SENSOR SYSTEM, AND METHOD FOR CALIBRATING THE SENSOR SYSTEM

CROSS REFERENCE TO RELATED APPLICATIONS

This application is based upon and claims the benefit of priority from Japanese patent application No. 2018-161365, filed on Aug. 30, 2018, the disclosure of which is incorporated herein in its entirety by reference.

BACKGROUND

The present disclosure relates to a sensor system, a robot hand, a method for calibrating a sensor system, and a program.

Development of a kinesthetic-sense sensor that detects pressures in a plurality of axial directions and moments around a plurality of axes has been underway. Further, there has been a proposal that a sensor system be constructed by using a plurality of such kinesthetic-sense sensors and applied to robot hands and the like.

For example, Japanese Unexamined Patent Application Publication No. 2011-158404 discloses a physical-quantity derivation apparatus and the like capable of deriving information about a physical quantity acting on a contact member of a kinesthetic-sense sensor in the horizontal direction.

SUMMARY

In the case in which a force applied from an object is detected by using such a kinesthetic-sense sensor, when the applied force exceeds the range in which an installed sensor system can detect the force, i.e., when the applied force exceeds the dynamic range of the sensor system, the sensor system cannot correctly detect the applied force. However, in order to expand the dynamic range of the sensor system, it is necessary to change the mechanical characteristics of the kinesthetic-sense sensor or adopt a structure by which the dynamic range is expanded at the sacrifice of the resolution. It is burdensome for the designer of a sensor system to select an optimal kinesthetic-sense sensor each time the dynamic range of the sensor system is changed. Further, adopting a structure by which the dynamic range is expanded at the sacrifice of the resolution is not desirable as the design of the sensor system.

The present disclosure has been made to solve the above-described problem and an object thereof is to provide, for example, a sensor system capable of easily expanding its dynamic range while preventing or minimizing a decrease in the resolution with which an applied force is detected.

A first exemplary aspect is a sensor system including: a substrate having a reference plane; a plurality of kinesthetic-sense sensors disposed on the substrate, each of the plurality of kinesthetic-sense sensors being configured to output signals of three axial directions corresponding to an orthogonal-axis direction orthogonal to the reference plane and two axial directions parallel to the reference plane, respectively, according to an external force from an object received at a force receiving part; a control unit configured to determine whether or not a value of each of the signals is larger than a predetermined threshold and calculate a pressing force in the orthogonal-axis direction or a moment around the orthogonal axis received from the object based on a result of the determination; and an output unit configured to output a result of the calculation.

By the above-described configuration, the sensor system can first select, from signals acquired from a plurality of kinesthetic-sense sensors, signals for calculation (hereinafter also referred to as calculation signals) used for the calculation of a pressing force in the orthogonal-axis direction or a moment around the orthogonal axis, and then calculate the pressing force or the moment.

In the above-described sensor system, the plurality of kinesthetic-sense sensors may be capacitance-type sensors. In this way, the sensor system can appropriately calculate the pressing force or the moment.

In the above-described sensor system, the substrate may include a projection part including a top surface parallel to the reference plane, and the plurality of kinesthetic-sense sensors may be disposed on the reference plane and the top surface, respectively. In this way, the dynamic range of the sensor system can be expanded while preventing or minimizing the decrease in the resolution.

In the above-described sensor system, the projection part may be compressible in the orthogonal-axis direction. In this way, the dynamic range of the sensor system can be appropriately expanded.

The sensor system may further include a contact part tightly connected to the force receiving part and including a contact surface configured to come into contact with the object when the object is grasped. The plurality of kinesthetic-sense sensors may include first and second kinesthetic-sense sensors. A height from the contact surface of the contact part tightly connected to the force receiving part of the first kinesthetic-sense sensor to the reference plane may be larger than a height from the contact surface of the contact part tightly connected to the force receiving part of the second kinesthetic-sense sensor to the reference plane. By the above-described configuration, it is possible to provide a sensor system which can be easily assembled and whose dynamic range can be easily expanded.

In the above-described sensor system, the contact part may be compressible in the orthogonal-axis direction. In this way, the dynamic range of the sensor system can be appropriately expanded.

In the above-described sensor system, the control unit may perform the calculation based on signals output by at least one of the plurality of kinesthetic-sense sensors of which all the signals corresponding to the three axial directions are equal to or smaller than the threshold. In this way, it is possible to perform a more accurate calculation.

In the sensor system, the control unit may calculate the pressing force in the orthogonal-axis direction based on signals output by at least one of the plurality of kinesthetic-sense sensors that has output signals no larger than the threshold among the signals corresponding to the orthogonal-axis direction output by the plurality of kinesthetic-sense sensors. In this way, it is possible to calculate the pressing force more accurately.

Another exemplary aspect is a robot hand including: a plurality of grasping parts each including the substrate and the plurality of kinesthetic-sense sensors, the grasping parts being configured to grasp an object; a driving unit configured to move the plurality of grasping parts toward each other so that the grasping parts are opposed to each other; and any one of the above-described sensor systems. In this way, the dynamic range of the robot hand can be expanded while preventing the decrease in the resolution.

Another exemplary aspect is a method for calibrating a sensor system, including: grasping a reference object for calibration; controlling a posture of the robot hand so that the reference plane becomes parallel or perpendicular to a gravitational direction; determining whether or not calibration should be performed for the calculation result output by the sensor system in the controlled posture; and setting a calibration value used for calibrating the output based on the determination. In this way, it is possible to easily calibrate the kinesthetic-sense sensor.

Another exemplary aspect is a sensor-system calibration program for causing a computer to perform a method for calibrating a sensor system, the method including: grasping a reference object for calibration; controlling a posture of the robot hand so that the reference plane becomes parallel or perpendicular to a gravitational direction; determining whether or not calibration should be performed for the calculation result output by the sensor system in the controlled posture; and setting a calibration value used for calibrating the output based on the determination. In this way, it is possible to easily calibrate the kinesthetic-sense sensor.

According to the present disclosure, it is possible to provide, for example, a sensor system capable of easily expanding its dynamic range while preventing or minimizing a decrease in the resolution with which an applied force is detected.

The above and other objects, features and advantages of the present disclosure will become more fully understood from the detailed description given hereinbelow and the accompanying drawings which are given by way of illustration only, and thus are not to be considered as limiting the present disclosure.

BRIEF DESCRIPTION OF DRAWINGS

FIG. 5 is a cross section of a kinesthetic-sense sensor as viewed from an xz-plane;

and

Figure 23:
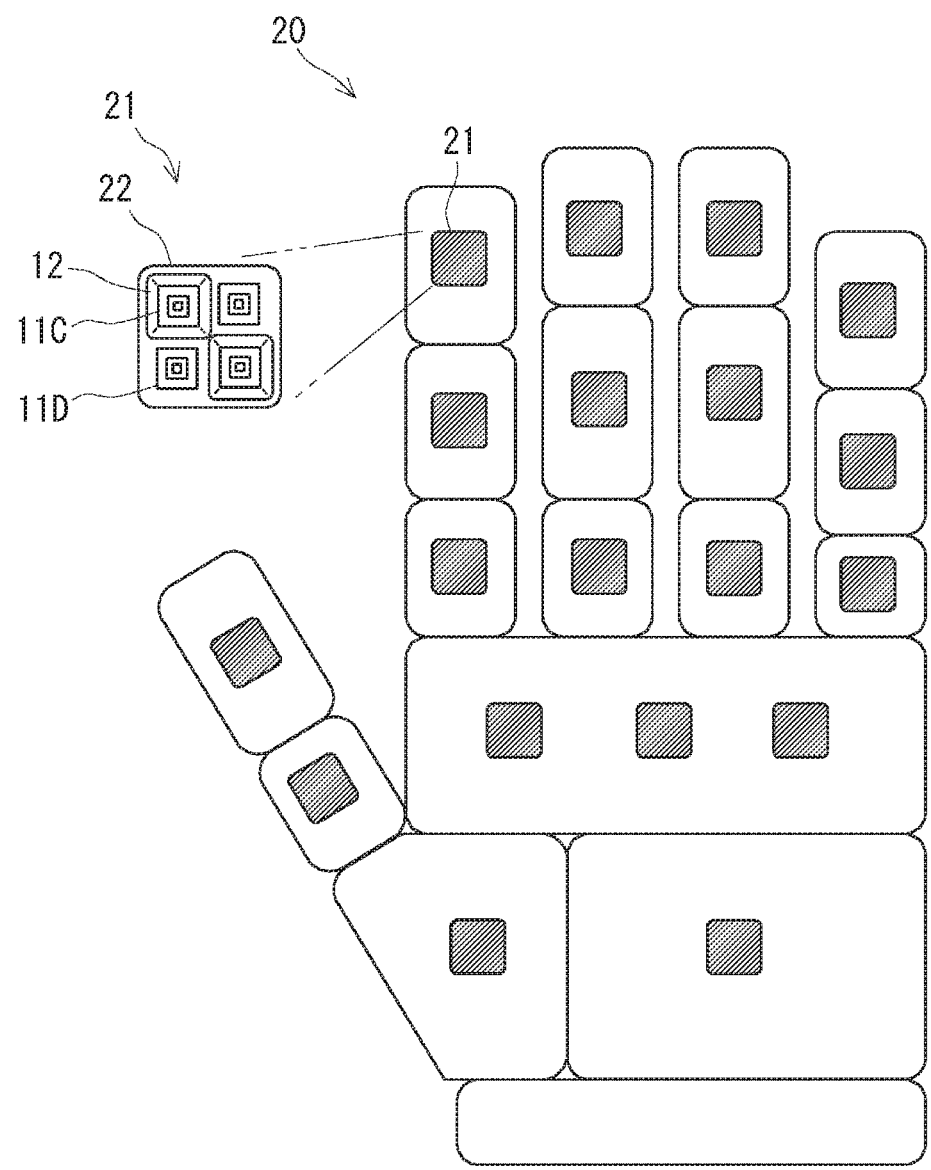

FIG. 23 is a diagram for explaining a modified example 4 of the embodiment.

DETAILED DESCRIPTION

Hereinafter, the present disclosure will be explained through embodiments of the present disclosure. However, they are not intended to limit the scope of the present disclosure according to the claims. Further, all of the components/structures described in the embodiments are not necessarily indispensable as means for solving the problem.

Figure 1:
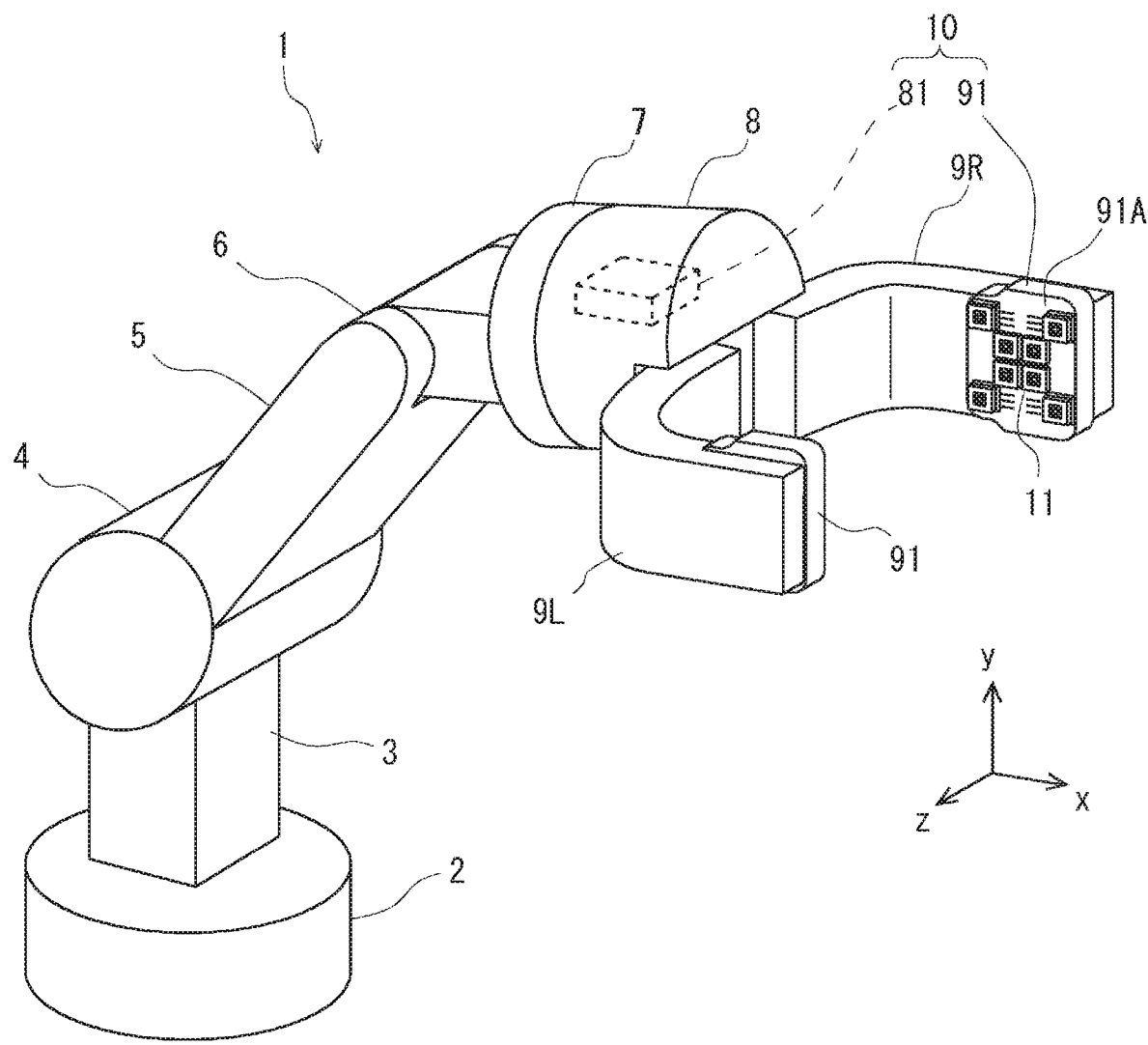
FIG. 1 is a perspective view of an external appearance of a robot hand according to an embodiment.

FIG. 1 is a perspective view of an external appearance of a robot hand 1 according to an embodiment. Note that for the sake of explaining a positional relation among components, a right-handed orthogonal coordinate system is shown in FIG. 1. Further, in FIG. 2 and subsequent figures, when an orthogonal coordinate system is shown, x-, y- and z-axial directions in the orthogonal coordinate system coincide with those of the coordinate system shown in FIG. 1.

The robot hand 1 is an apparatus that grasps an object and moves grasped object to a predetermined place. The robot hand 1 includes, as its main components, a pedestal 2, a first arm 3, a first joint 4, a second arm 5, a second joint 6, a third arm 7, a third joint 8, a first finger part 9R, and a second finger part 9L.

The pedestal 2 is a support base that is fixed in an arbitrary place and supports the whole robot hand 1. The pedestal 2 has a stubby cylindrical shape and its circular bottom surface is mounted on an arbitrary mounting surface. Further, the first arm 3 is connected to the top surface of the pedestal 2. The first arm 3 is a rod-like member extending upward from the pedestal 2 and its upper end is connected to the first joint 4.

The first joint 4 is connected to each of the first arm 3 and the second arm 5, and enables the first and second arms 3 and 5 to rotate relative to each other around a rotation axis parallel to the XZ-plane within a predetermined range. The first joint 4 includes a motor for rotating the first and second arms 3 and 5 relative to each other. The second arm 5 is a rod-like member connected at one end to the first joint 4. The second arm 5 extends from the first joint 4 in a direction perpendicular to the rotation axis of the first joint 4 and is connected at the other end to the second joint 6.

The second joint 6 is connected to each of the second arm 5 and the third arm 7, and enables the second and third arms 5 and 7 to rotate relative to each other around a rotation axis parallel to the XZ-plane within a predetermined range. The second joint 6 includes a motor for rotating the second and third arms 5 and 7 relative to each other. The third arm 7 is a rod-like member connected at one end to the second joint 6. The third arm 7 extends from the second joint 6 in a direction perpendicular to the rotation axis of the second joint 6 and is connected at the other end to the third joint 8.

The third joint 8 is connected to the third arm 7 and rotates around an axis perpendicular to the rotation axis of the second joint 6. The third joint 8 includes a motor for rotating it around the axis perpendicular to the rotation axis of the second joint 6. Further, the first finger part 9R and the second finger part 9L are connected on the side of the third joint 8 opposite to the side thereof connected to the third arm 7. The third joint 8 includes a driving unit for moving the first and second finger parts 9R and 9L toward each other and away from each other.

The third joint 8 also includes a signal processing unit 81 which is a substrate including an arithmetic device such as a CPU (Central Processing Unit). The signal processing unit 81 is connected to a plurality of kinesthetic-sense sensors 11. The signal processing unit 81 acquires signals output from the kinesthetic-sense sensors 11, processes the acquired signals, and outputs a result of the processing.

The first and second finger parts 9R and 9L move away from each other and then move toward each other, and by doing so, have a function of grasping an object. The first and second finger parts 9R and 9L are connected at respective one ends to the third joint 8, extend from there in respective directions receding from each other, and bend at right angles in the same direction at middle parts thereof, so that the other ends thereof are opposed to each other. That is, each of the first and second finger parts 9R and 9L is a member having a roughly L-shape (or an inverted L-shape). Grasping parts 91 are provided in the tips of the first and second finger parts 9R and 9L so that they are opposed to each other. The plurality of kinesthetic-sense sensors 11 are mounted on (one or each of) reference planes 91A which are opposed surfaces of the grasping parts 91 included in the first and second finger parts 9R and 9L, respectively. The kinesthetic-sense sensors 11 are electrically connected to the signal processing unit 81 and supply signals which are output according to received external forces to the signal processing unit 81.

The robot hand 1 shown in FIG. 1 includes a sensor system 10. The sensor system 10 is a system that detects pressing forces in three axial directions and a moment around an axis orthogonal to the reference plane 91A (i.e., around the z-axis in FIG. 1), received from an object grasped by the robot hand 1, and outputs the detected pressing forces and the moment. The sensor system 10 includes the plurality of kinesthetic-sense sensors 11 included in the above-described grasping part 91, and has a function provided by the signal processing unit 81, i.e., a function of processing signals output by the kinesthetic-sense sensors 11. Details of the configuration of the sensor system 10 will be described later.

Figure 2:
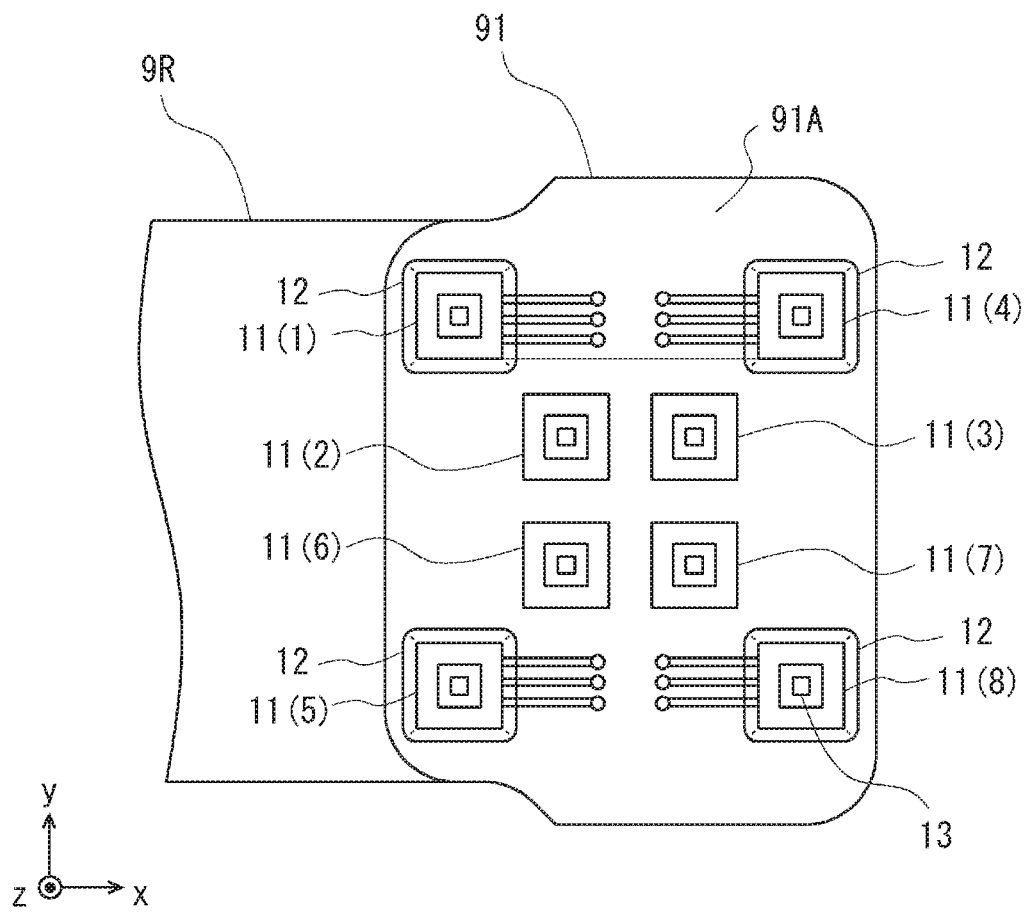
FIG. 2 shows a configuration of a grasping part.
Figure 3:
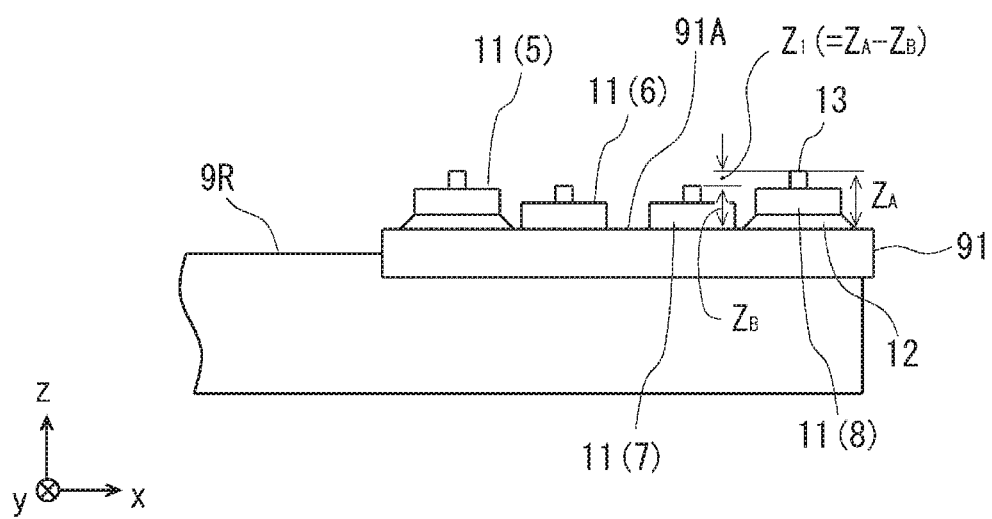
FIG. 3 shows a configuration of a grasping part.

Next, details of the grasping part 91 are described with reference to FIGS. 2 and 3. FIGS. 2 and 3 show a configuration of the grasping part 91. FIG. 2 shows a configuration of the tip of the first finger part 9R shown in FIG. 1 as viewed along the XY-plane from the z-axis positive side.

FIG. 3 shows the configuration of the grasping part 91 shown in FIG. 2 as viewed along the XZ-plane from the y-axis negative side.

The grasping part 91 is a substrate on which a structure that comes into contact with an object when the robot hand grasps the object is disposed. The grasping part 91 is a substrate mainly made of, for example, glass, an epoxy resin, or the like. The grasping part 91 is formed of a substantially rectangular plate-like member and has a reference plane 91A on a side thereof that comes into contact with an object.

Four kinesthetic-sense sensors 11 are disposed in or near the center of the reference plane 91A in the grasping part 91. The kinesthetic-sense sensors 11 disposed on the reference plane 91A are mounted on the grasping part 91 so that they can communicate with the grasping part 91. Signals sent from the kinesthetic-sense sensors 11 to the grasping part 91 are supplied to the signal processing unit 81 through signal lines of the grasping part 91.

A projection part 12 is provided in or near each of the four corners of the reference plane 91A. Each of the projection parts 12 is a quadrangular-frustum member provided on the reference plane 91A. A bottom surface of each of the projection parts 12, which corresponds to the bottom side of the quadrangular frustum, is bonded to the reference plane 91A. Further, the kinesthetic-sense sensor 11 is disposed on the top surface of the projection part, which corresponds to the top side of the quadrangular frustum. In the projection part 12, a flexible substrate having flexibility is bonded to a surface of a material that is compressible in the z-axial direction and exerts a restoring force. Examples of the material that is compressible in the z-axial direction and exerts a restoring force include silicone rubber, urethane sponge, dome-shaped polycarbonate, etc. Note that the projection part 12 has such rigidity that when the force receiving part of the kinesthetic-sense sensor 11 receives an external force, it does not prevent the kinesthetic-sense sensor 11 from detecting the received external force. For example, when the kinesthetic-sense sensor 11 includes a flexible force receiving part, the projection part 12 has rigidity higher than that of the force receiving part.

The kinesthetic-sense sensor 11 is mounted on the flexible substrate bonded to the surface of the projection part 12. The projection part 12 is bonded on the reference plane 91A of the grasping part 91 so that it can be compressed. Consequently, the flexible substrate is connected to the grasping part 91 so that it does not hinder the compressing motion of the projection part 12 and can communicate with the grasping part 91. Signals sent from the kinesthetic-sense sensor 11 to the grasping part 91 through the flexible substrate are supplied to the signal processing unit 81 through signal lines of the grasping part 91.

As shown in FIG. 2, the grasping part 91 includes four kinesthetic-sense sensors 11(1), 11(4), 11(5) and 11(8) on the top surfaces of the projection parts 12 provided on the reference plane 91A, and includes another four kinesthetic-sense sensors 11(2), 11(3), 11(6) and 11(7) on the reference plane 91A.

The kinesthetic-sense sensor 11 is a sensor that receives an external force, and is an MEMS (Micro Electro Mechanical Systems) sensor that is constructed by using an MEMS technique. A contact part 13 that comes into contact with an object is provided in the central part of the kinesthetic-sense sensor 11. When the robot hand 1 grasps an object, the contact part 13 included in each kinesthetic-sense sensor 11 comes into contact with the object. The kinesthetic-sense sensor 11 outputs a signal corresponding to an external force received from the contact part 13. Note that details of the kinesthetic-sense sensor 11 will be described later.

As shown in FIG. 3, in the kinesthetic-sense sensor 11(7) disposed on the reference plane 91A, a height from the reference plane 91A to a contact surface of the contact part 13 is $Z_B$. Note that the contact surface means a surface of the contact part 13 that comes into contact with an object when the robot hand 1 grasps the object. That is, in FIG. 3, the contact surface is a surface on the z-axis positive side of the contact part 13. In the kinesthetic-sense sensor 11(8) disposed on the projection part 12, a height from the reference plane 91A to the contact surface of the contact part 13 is $Z_A$. As shown in FIG. 3, the height $Z_A$ related to the kinesthetic-sense sensor 11(8) disposed on the projection part 12 is larger than the height $Z_B$ related to the kinesthetic-sense sensor 11(7) disposed on the reference plane 91A by a height $Z_1$ of the projection part 12.

Figure 4:
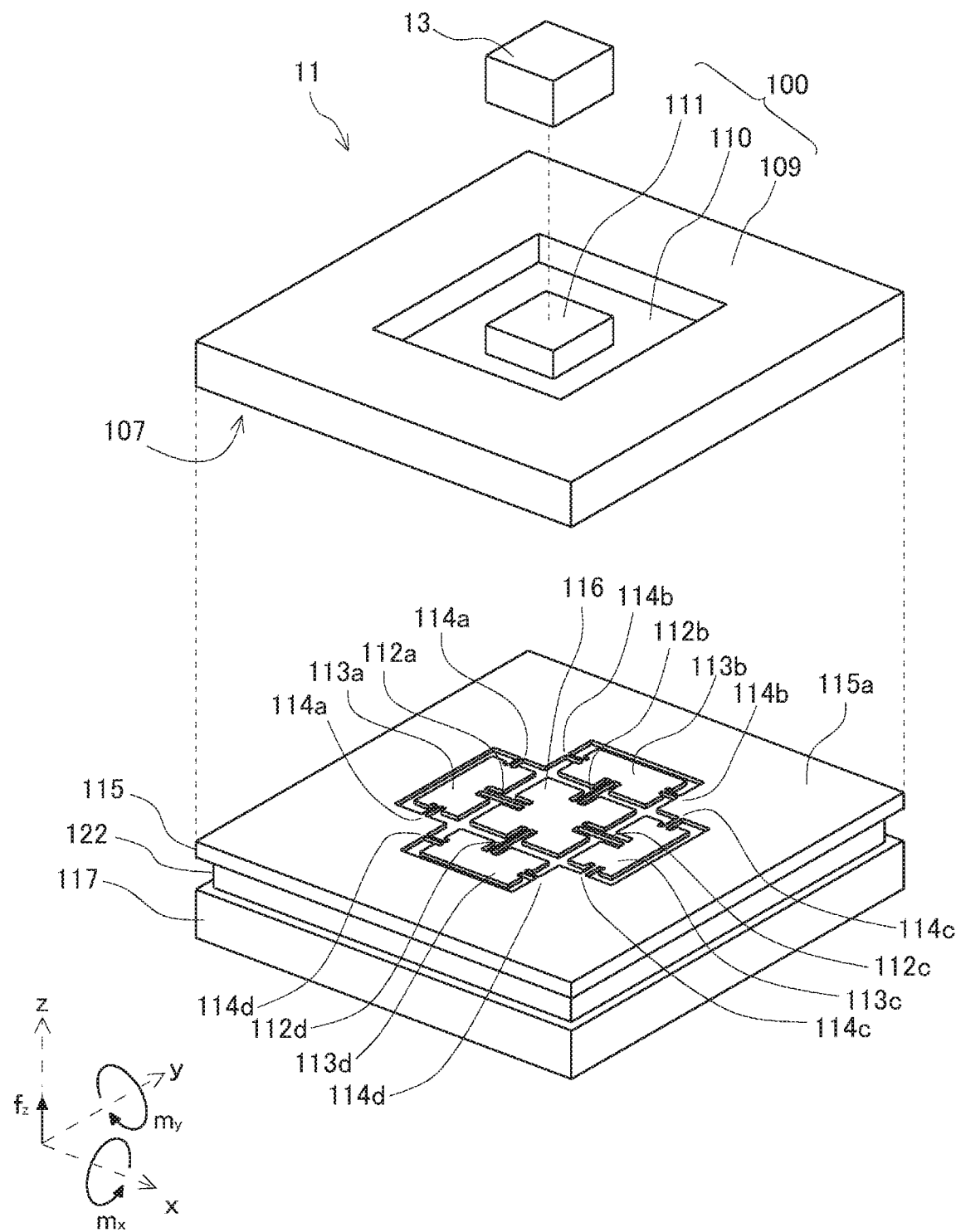
FIG. 4 is an exploded perspective view of a kinesthetic-sense sensor as viewed from a z-axis positive side.
Figure 7:
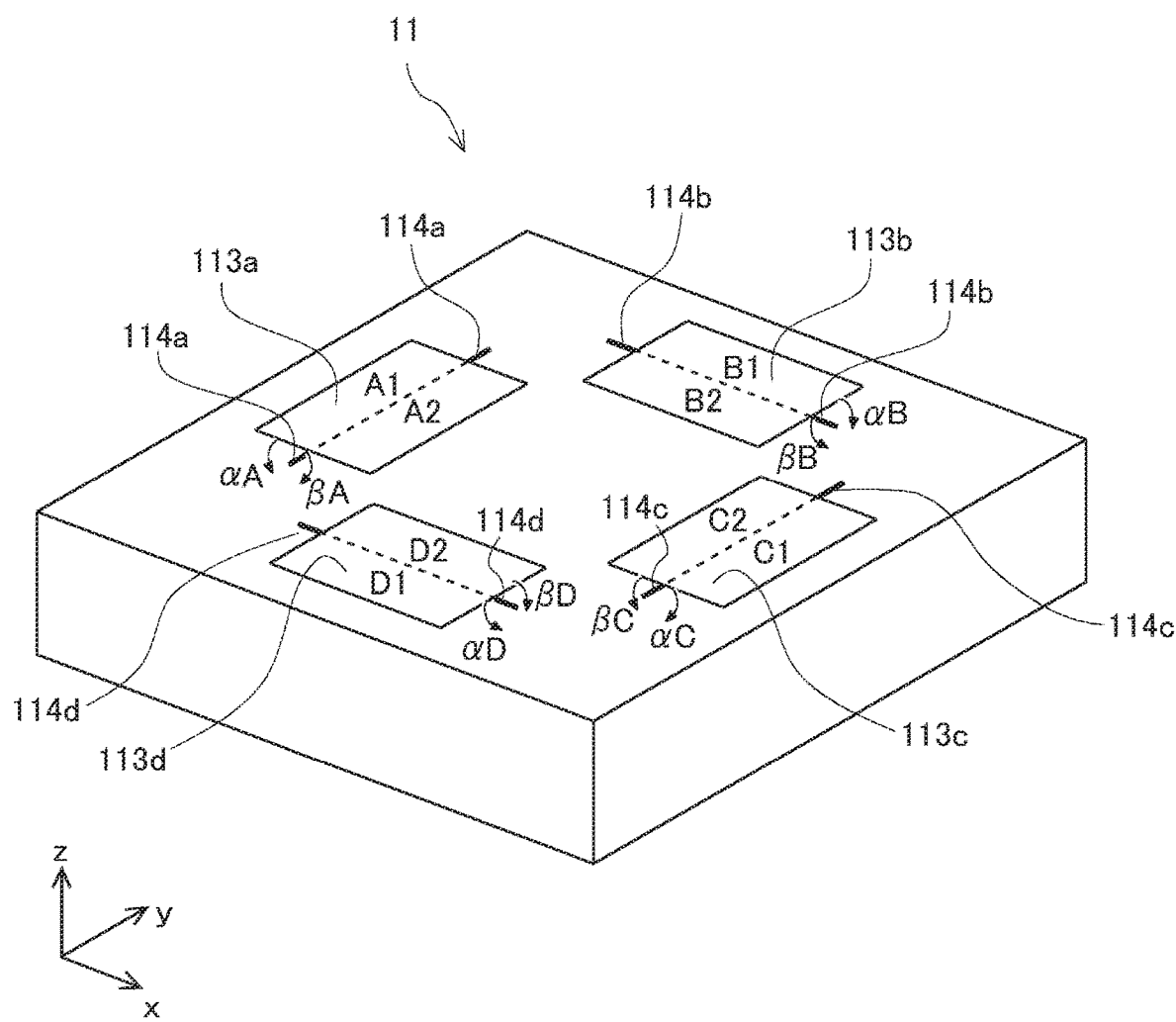
FIG. 7 is a perspective view for explaining a principle based on which a capacitance of a kinesthetic-sense sensor changes.

Next, the kinesthetic-sense sensor 11 is described with reference to FIGS. 4 and 7. FIG. 4 is an exploded perspective view of the kinesthetic-sense sensor 11 as viewed from the z-axis positive side. FIG. 5 is a cross section of the kinesthetic-sense sensor 11 as viewed from the xz-plane. The kinesthetic-sense sensor 11 has a quadrangular-prism shape with its surface perpendicular to the z-axis being a main surface. Further, the main surface is roughly square. The kinesthetic-sense sensor 11 is a capacitance-type sensor that outputs (signals corresponding to) pressing forces in the three axial directions. That is, the kinesthetic-sense sensor 11 includes a plurality of electrodes. The structure of the electrodes will be described later. The kinesthetic-sense sensor 11 includes, as its main components, a first silicon layer 100, a second silicon layer 115, a bonding part 122, and a sealing substrate 117.

The first silicon layer 100 also serves as a support substrate that supports a seesaw part (which will be described later). Further, the first silicon layer 100 is a conductive silicon layer. The first silicon layer 100 includes a diaphragm 110 formed in a central part of its rear surface. Further, a force receiving part 111, which is formed in the form of a protrusion, is formed in a central part on the inner side of the diaphragm 110. Similarly to the outer shape of the first silicon layer 100, each of the diaphragm 110 and the force receiving part 111 has a roughly square shape on the plan view. The diaphragm 110 is a thin part having a thickness smaller than that of a peripheral part 109 of the first silicon layer 100. Further, the diaphragm 110 is flexible and elastically deforms according to a force applied to the force receiving part 111. The first silicon layer 100 originally has a predetermined thickness. Then, by etching a central part of the first silicon layer 100 except for the force receiving part 111 from the Z-axis positive side and thereby reducing the thickness of that part, the diaphragm 110 is formed in the first silicon layer 100. Note that the force receiving part 111 may have a thickness equal to that of the peripheral part 109, or a thickness larger than that of the peripheral part 109. The force receiving part 111 is constructed by connecting a contact part 13 on the top surface of a first force receiving part so that an external force is received through the contact part 13.

In the second silicon layer 115, which is located on the lower-surface side of the first silicon layer 100, a force receiving piece 116 is formed in its central part and four seesaw parts 113a to 113d are formed around the force receiving piece 116. The seesaw parts 113a and 113c are disposed on both sides of the force receiving piece 116 in the x-axis direction, and the seesaw parts 113b and 113d are disposed on both sides of the force receiving piece 116 in the y-axis direction. The force receiving piece 116 is connected to the seesaw parts 113a to 113d through hinge beams 112a to 112d, respectively (each of them is also referred to as a hinge beam 112).

The second silicon layer 115 originally has a predetermined thickness. Then, by etching it, the force receiving piece 116, the seesaw parts 113a to 113d, the hinge beams 112a to 112d, etc. are formed in the second silicon layer 115. Similarly to the first silicon layer 100, the second silicon layer 115 is a conductive silicon layer. Further, the whole of the force receiving piece 116, the seesaw parts 113a to 113d, the hinge beams 112a to 112d, etc. are conductive and electrically connected to each other.

An insulating layer 107 is disposed between the first silicon layer 100 and the second silicon layer 115. The insulating layer 107 is processed by sacrificial etching and thereby joins a peripheral part 115a of the second silicon layer 115 with the first silicon layer 100. Further, the insulating layer 107 joins the force receiving part 111 with the force receiving piece 116.

A torsion beam 114a extends in parallel and coaxially with the y-axis from each of both sides of the seesaw part 113a on the y-axis positive and negative sides. A torsion beam 114b extends in parallel and coaxially with the x-axis from each of both sides of the seesaw part 113b on the x-axis positive and negative sides. A torsion beam 114c extends in parallel and coaxially with the y-axis from each of both sides of the seesaw part 113c on the y-axis positive and negative sides. A torsion beam 114d extends in parallel and coaxially with the x-axis from each of both sides of the seesaw part 113d on the x-axis positive and negative sides. The seesaw parts 113a to 113d are connected to the peripheral part 115a through the torsion beams 114a to 114d, respectively. The torsion beams 114a to 114d are formed as beam structures so that they can be twisted. Therefore, the seesaw parts 113a to 113d are supported so that they can rotate by using the torsion beams 114a to 114d, by which the seesaw parts 113a to 113d are respectively supported, as their rotation axes. The torsion beams 114a to 114d may also be referred to as the rotational axes of the seesaw parts 113a to 113d, respectively.

The second silicon layer 115 includes the peripheral part 115a formed around the seesaw parts 113a to 113d. The peripheral part 115a supports, by being connected to the torsion beams 114a to 114d, the seesaw parts 113.

On the x-axis negative side of the force receiving piece 116, the opposed sides of the force receiving piece 116 and the seesaw part 113a are connected to each other at their central parts through the hinge beam 112a. On the y-axis positive side of the force receiving piece 116, the opposed sides of the force receiving piece 116 and the seesaw part 113b are connected to each other at their central parts through the hinge beam 112b. On the x-axis positive side of the force receiving piece 116, the central parts of the opposed sides of the force receiving piece 116 and the seesaw part 113c are connected to each other through the hinge beam 112c. On the y-axis negative side of the force receiving piece 116, the central parts of the opposed sides of the force receiving piece 116 and the seesaw part 113d are connected to each other through the hinge beam 112d. The hinge beams 112a and 112c are disposed in parallel and coaxially with the x-axis. The hinge beams 112b and 112d are disposed in parallel and coaxially with the y-axis. The hinge beams 112a to 112d are formed as beam structures so that they can be warped and twisted, and they extend perpendicular to the rotation axes formed by the torsion beams 114a to 114d, respectively.

By the above-described configuration, the force receiving piece 116 is supported so that it can rotate by using the hinge beams 112a and 112c as its rotation axis. Further, the force receiving piece 116 is supported so that it can rotate by using the hinge beams 112b and 112d as its rotation axis. Further, the force receiving piece 116 is supported so that it can be displaced in parallel to the z-axis direction. In other words, the force receiving piece 116 follow and move in the z-axis direction, around the x-axis, and around the y-axis according to an external force received by the force receiving part 111. Further, the force receiving part 111 transfers the external force to the seesaw parts 113a to 113d. When the seesaw parts 113a to 113d are displaced in the rotational direction by the transferred external force, the kinesthetic-sense sensor 11 outputs (signals corresponding to) pressing forces in the three axial directions that the kinesthetic-sense sensor 11 has received.

Through electrodes 121 are formed in the peripheral part 115a of the second silicon layer 115, which are located on the outer sides of the seesaw parts 113a to 113d. The through electrodes 121 penetrate the second silicon layer 115 and the insulating layer 107, and electrically connect the first silicon layer 100, the second silicon layer 115, and the bonding part 122 with one another.

The bonding part 122 seals and joins the second silicon layer 115 and the sealing substrate 117 in the peripheral part of the kinesthetic-sense sensor 11 so as to surround the seesaw parts 113 and the force receiving piece 116. The bonding part 122 is a conductive metal diffusion joining member and is made of, for example, a Cu—Sn (copper-tin) alloy or the like.

The sealing substrate 117 is a substrate that seals the whole moveable part including the seesaw parts 113a to 113d and the force receiving piece 116. The sealing substrate 117 may be, for example, a silicon substrate, an LTCC (Low Temperature Co-fired Ceramic) substrate, an LSI (Large Scale Integration), or the like. For example, vias (not shown) that draw out an electric potential at electrodes located on the upper-surface side of the sealing substrate 117 to the lower-surface side thereof are disposed in the sealing substrate 117. Further, external terminals (not shown) connected to these vias are disposed on the rear surface (i.e., the lower-surface side) of the sealing substrate 117 and an external detection circuit or the like is connected to these external terminals. Further, circuits such as a detection circuit and wiring lines are disposed as required inside the sealing substrate 117. The sealing substrate 117 may be preferably formed by an LSI. In this way, a processing circuit can be disposed near the sensor structure, thereby making the sensor less susceptible to noises.

Fixed electrode pairs 120a to 120d are formed on the upper-surface side of the sealing substrate 117. The fixed electrode pair 120a includes fixed electrodes 118a and 119a. Similarly, the fixed electrode pair 120b includes fixed electrodes 118b and 119b, and the fixed electrode pair 120c includes fixed electrodes 118c and 119c. Further, the fixed electrode pair 120d includes fixed electrodes 118d and 119d.

The fixed electrodes 118a to 118d and 119a to 119d are conductive films such as metal and are formed on the sealing substrate 117 by patterning. The fixed electrodes 118a to 118d and 119a to 119d are disposed at positions corresponding to the seesaw parts 113a to 113d, respectively, and constitute capacitive elements with the seesaw parts 113a to 113d. The fixed electrodes 118a to 118d are disposed on the outer side with respect to the rotational axes (the torsion beams 114a to 114d) of the seesaw parts 113a to 113d, and the fixed electrodes 119a to 119d are disposed on the inner side. For example, capacitances of these capacitive elements can be detected by an external detection circuit or the like through the vias (not shown) disposed in the sealing substrate 117, or by an LSI formed inside the sealing substrate 117.

Figure 6A:
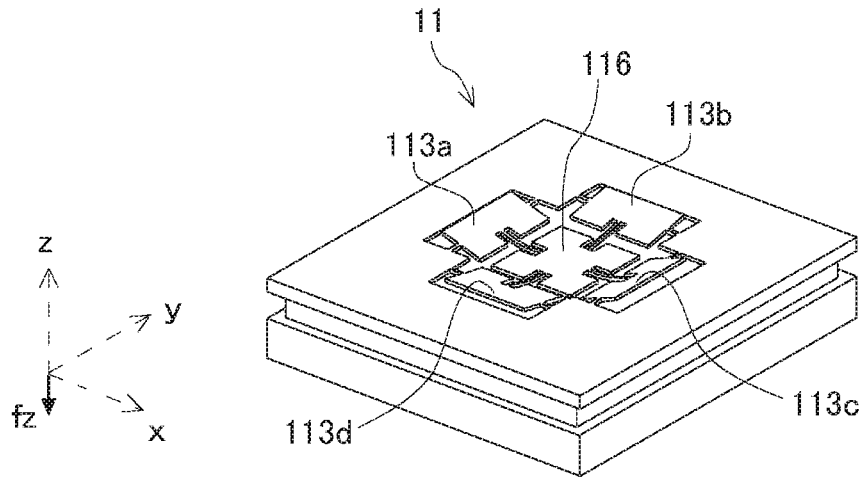
FIG. 6A is a perspective view for explaining movements of movable parts of a kinesthetic-sense sensor.
Figure 6B:
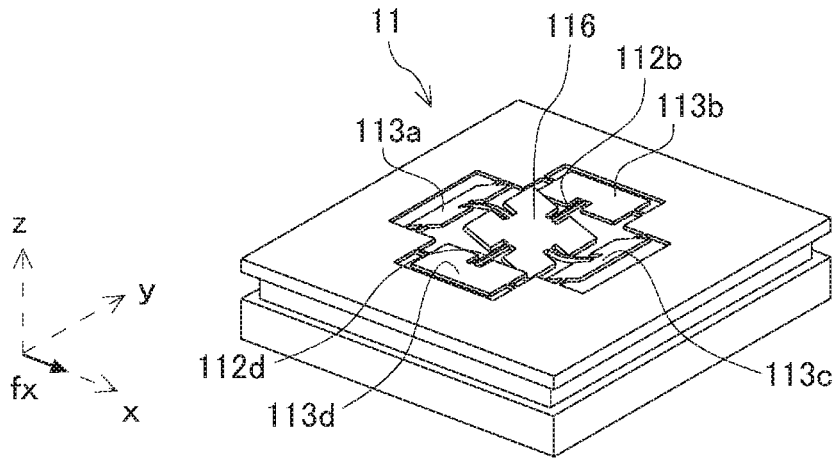
FIG. 6B is a perspective view for explaining movements of movable parts of a kinesthetic-sense sensor.
Figure 6C:
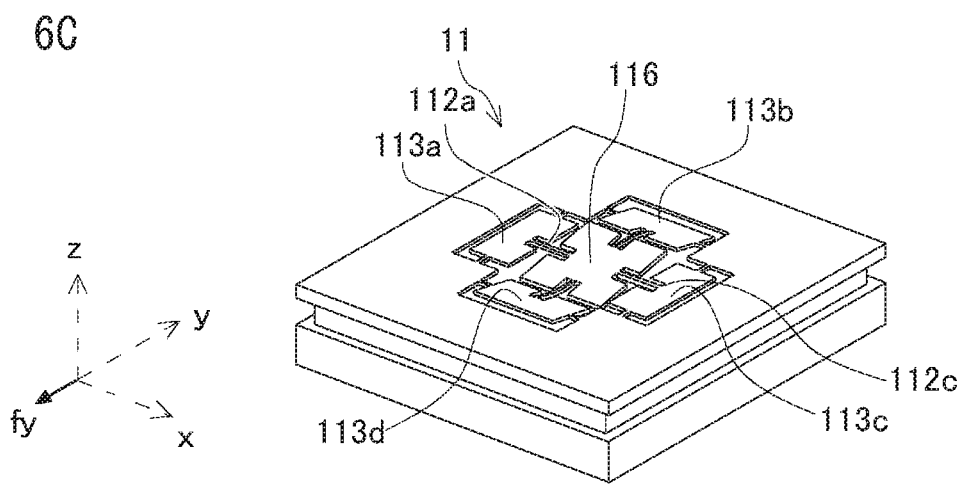
FIG. 6C is a perspective view for explaining movements of movable parts of a kinesthetic-sense sensor.

Next, movements of the moveable part of the kinesthetic-sense sensor 11 are described in detail with reference to FIGS. 6A to 6C. FIGS. 6A to 6C are perspective views for explaining movements of the kinesthetic-sense sensor. FIG. 6A shows a case where a pressing force fz in the z-axis negative direction is applied to the force receiving part 111. FIG. 6B shows a case where a pressing force fx in the x-axis positive direction is applied to the force receiving part 111. FIG. 6C shows a case where a pressing force fy in the y-axis negative direction is applied to the force receiving part 111. Note that in FIGS. 6A to 6C, illustration of the first silicon layer 100 is omitted for the sake of explanation.

As shown in FIG. 6A, when the pressing force fz in the z-axis negative direction is applied to the force receiving part 111, the force receiving part 111 and the force receiving piece 116 joined to the force receiving part 111 are displaced in the z-axis negative direction while remaining parallel to the xy-plane. As a result, the seesaw part 113a rotates so that the x-axis positive side thereof inclines to the z-axis negative side. Similarly, the seesaw part 113b rotates so that the y-axis negative side thereof inclines to the z-axis negative side, and the seesaw part 113c rotates so that the x-axis negative side thereof inclines to the z-axis negative side. Further, the seesaw part 113d rotates so that the y-axis positive side thereof inclines to the z-axis negative side.

As shown in FIG. 6B, when the pressing force fx in the x-axis positive direction is applied to the force receiving part 111, the first force receiving part 111 rotates around the y-axis and also rotates the force receiving piece 116. Further, since the seesaw parts 113b and 113d do not rotate and each of the hinge beams 112b and 112d is twisted, they serve as supporting points for the rotational motion of the force receiving part 111. Meanwhile, the seesaw parts 113a and 113c follow the movement of the force receiving part 111 and thereby rotate in a direction opposite to the rotational direction of the force receiving part 111. In FIG. 6B, the force receiving part 111 rotates so that the x-axis positive side thereof inclines to the z-axis negative side. Therefore, the seesaw parts 113a and 113c rotate so that the x-axis negative sides thereof incline to the z-axis negative side.

As shown in FIG. 6C, when the pressing force fy in the y-axis negative direction is applied to the force receiving part 111, the first force receiving part 111 rotates around the x-axis and also rotates the force receiving piece 116. Further, since the seesaw parts 113a and 113c do not rotate and each of the hinge beams 112a and 112c is twisted, they serve as supporting points for the rotational motion of the force receiving part 111. Meanwhile, the seesaw parts 113b and 113d follow the movement of the force receiving part 111 and thereby rotate in a direction opposite to the rotational direction of the force receiving part 111. In FIG. 6C, the force receiving part 111 rotates so that the y-axis negative side thereof inclines to the z-axis negative side. Therefore, the seesaw parts 113b and 113d rotate so that the y-axis positive sides thereof incline to the z-axis negative side.

Next, outputs of the kinesthetic-sense sensor 11 are described with reference to FIG. 7. FIG. 7 is a perspective view for explaining a principle based on which the capacitance of the kinesthetic-sense sensor changes. FIG. 7 shows an example of an arrangement of the seesaw parts 113a to 113d and the torsion beams 114a to 114d in the kinesthetic-sense sensor 11.

Firstly, a change in the capacitance of the electrode corresponding to the seesaw part 113*a* is described. The capacitance of each of the seesaw parts 113*a* to 113*d* included in the kinesthetic-sense sensor 11 is changed based on a principle similar to that described below for the seesaw part 113*a*.

In the seesaw part 113*a*, the torsion beams 114*a*, which serve as the rotational axis of the seesaw part 113*a*, extend in the y-axis direction. Therefore, the seesaw part 113*a* rotates around the torsion beams 114*a* in an αA direction or a βA direction according to forces applied in the x- and z-axis directions. The capacitance on the outer side of the rotational axis of the seesaw part 113*a* is referred to as a capacitance A1 and the capacitance on the inner side of the rotational axis is referred to as a capacitance A2. When the seesaw part 113*a* rotates in the αA direction, the capacitance A1 decreases while the capacitance A2 increases. Further, when the seesaw part 113*a* rotates in the βA direction, the capacitance A1 increases while the capacitance A2 decreases. That is, the kinesthetic-sense sensor 11 includes an electrode that detects the capacitance A1, which is the capacitance on the outer side of the seesaw part 113*a*, and an electrode that detects the capacitance A2, which is the capacitance on the inner side of the seesaw part 113*a*. In this way, the kinesthetic-sense sensor 11 detects a difference between the capacitances A1 and A2 according to the rotational displacement of the seesaw part 113*a*.

The seesaw part 113*a* rotates in the αA direction when a force in the z-axis positive direction is applied to the force receiving part 111, and rotates in the βA direction when a force in the z-axis negative direction is applied to the force receiving part 111. The seesaw part 113*a* rotates in the βA direction when a force in the x-axis negative direction is applied to the force receiving part 111, and rotates in the αA direction when a force in the x-axis positive direction is applied to the force receiving part 111. The seesaw part 113*a* is not displaced when a force in the y-axis direction is applied.

Based on a principle similar to that explained above, the seesaw part 113*b* rotates in the αB direction and the βB direction by using the torsion beams 114*b* extending in the x-axis direction as its rotational axis. As a result of this rotation, capacitances B1 and B2 corresponding to the seesaw part 113*b* change. Similarly, the seesaw part 113*c* rotates in the αC direction and the PC direction by using the torsion beams 114*c* extending in the y-axis direction as its rotational axis. As a result of this rotation, capacitances C1 and C2 corresponding to the seesaw part 113*c* change. The seesaw part 113*d* rotates in the αD direction and the βD direction by using the torsion beams 114*d* extending in the x-axis direction as its rotational axis. As a result of this rotation, capacitances D1 and D2 corresponding to the seesaw part 113*d* change. In this way, the kinesthetic-sense sensor 11 detects differences between the electrodes included the respective seesaw parts 113*a* to 113*d*. The differences between the electrodes detected by the kinesthetic-sense sensor 11 are converted into pressing forces in the three axial directions by the below-shown Expression (1).

[Expression 1]

$$\begin{pmatrix} fx \\ fy \\ fz \\ 0 \end{pmatrix} = \frac{1}{4} \cdot \begin{pmatrix} 2 & 0 & -2 & 0 \\ 0 & 2 & 0 & -2 \\ 1 & 1 & 1 & 1 \\ 0 & 0 & 0 & 0 \end{pmatrix} \cdot \begin{pmatrix} A1 - A2 \\ B1 - B2 \\ C1 - C2 \\ D1 - D2 \end{pmatrix} \quad (1)$$

In the expression, fx is a pressing force in the x-axis direction received by the force receiving part 111; fy is a pressing force in the y-axis direction received by the force receiving part 111; and fz is a pressing force in the z-axis direction received by the force receiving part 111. The calculation expressed by Expression (1) can be implemented by hardware including an analogue circuit or a digital circuit, software, or both of them. For example, an arithmetic circuit that performs the calculation expressed by Expression (1) may be disposed inside the substrate (the grasping part 91), or may be implemented by an external microcomputer or the like. The kinesthetic-sense sensor may be integrated with the semiconductor substrate. By integrating the kinesthetic-sense sensor with the semiconductor substrate, the arithmetic function can be incorporated into the semiconductor substrate, thereby making it possible to reduce the size of the sensor system even further. Further, an improvement in the S/N ratio can also be expected.

As described above, the kinesthetic-sense sensor 11 includes the force receiving part 111 that follows and moves in the z-axis direction, around the x-axis, and around the y-axis according to an external force. Further, the kinesthetic-sense sensor 11 outputs an external force received by the force receiving part 111 as (signals corresponding to) pressing forces (fx, fy, fz) in the three axial directions.

Note that the configuration of the kinesthetic-sense sensor 11 described above is an example of a configuration of a sensor and specific configurations thereof are not limited to this example. For example, the number of seesaw parts connected to the force receiving part 111 may be three instead of four.

Details of the kinesthetic-sense sensor 11 have been described above. By arranging a plurality of kinesthetic-sense sensors 11 each of which outputs an external force received by its force receiving part 111 as pressing forces (fx, fy, fz) in the three axial directions, the sensor system 10 can detect pressing forces in the three axial directions and a moment around the axis orthogonal to the reference plane 91A, applied from an object and received by the grasping part 91.

Figure 8:
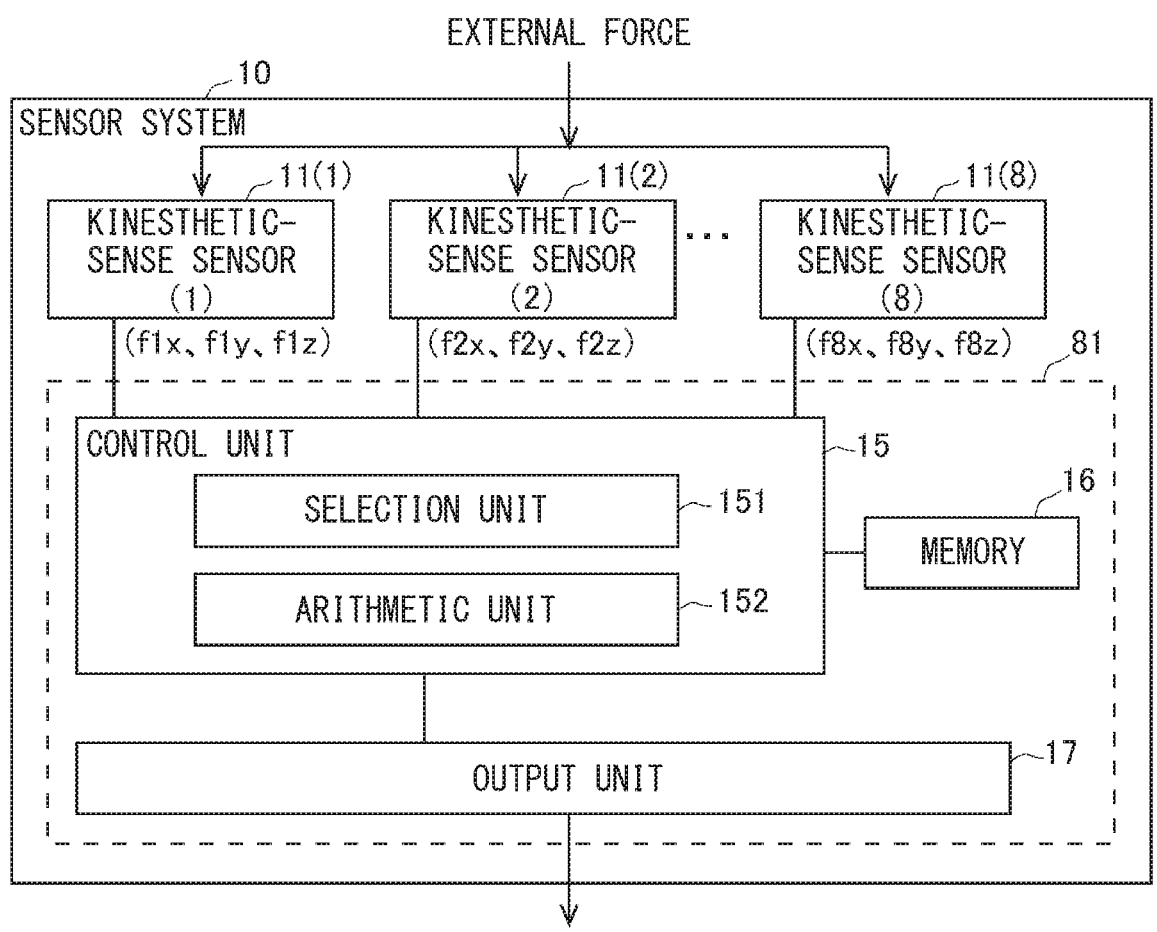
FIG. 8 is a functional block diagram of a sensor system according to an embodiment.

Next, a functional configuration of the sensor system 10 is described with reference to FIG. 8. FIG. 8 is a functional block diagram of a sensor system according to an embodiment. The sensor system 10 includes a plurality of kinesthetic-sense sensors 11 and a signal processing unit 81. The kinesthetic-sense sensors 11 are the above-described eight kinesthetic-sense sensors 11(1) to 11(8) provided in the grasping part 91.

The signal processing unit 81 includes a control unit 15, and a memory 16, and an output unit 17. The control unit 15 is an arithmetic device including a CPU mounted on a substrate. The control unit 15 receives outputs of the kinesthetic-sense sensors 11, performs calculations while referring to data stored in the memory 16, and supplies results of the performed calculations to the output unit 17.

The control unit 15 includes a selection unit 151 and an arithmetic unit 152. The selection unit 151 determines whether or not a signal received from the kinesthetic-sense sensor 11 is larger than a predetermined threshold. The threshold is stored in the memory 16 in advance. Further, the selection unit 151 selects calculation signals used for the calculation of a pressing force in the direction perpendicular to the reference plane 91A or a moment around the axis perpendicular to the reference plane 91A based on the determination result. The arithmetic unit 152 calculates pressing forces in the three axial directions and the moment around the axis perpendicular to the reference plane 91A, applied from an object and received by the grasping part 91 based on the calculation signals selected by the selection unit 151.

The output unit 17 is an interface unit for externally outputting certain signals. The interface unit consists of, for example, connectors mounted on the substrate. The output unit 17 receives the calculation result from the control unit 15 and outputs the received result. The output unit 17 is not limited to wired connectors, and may be a wireless communication interface.

Figure 9:
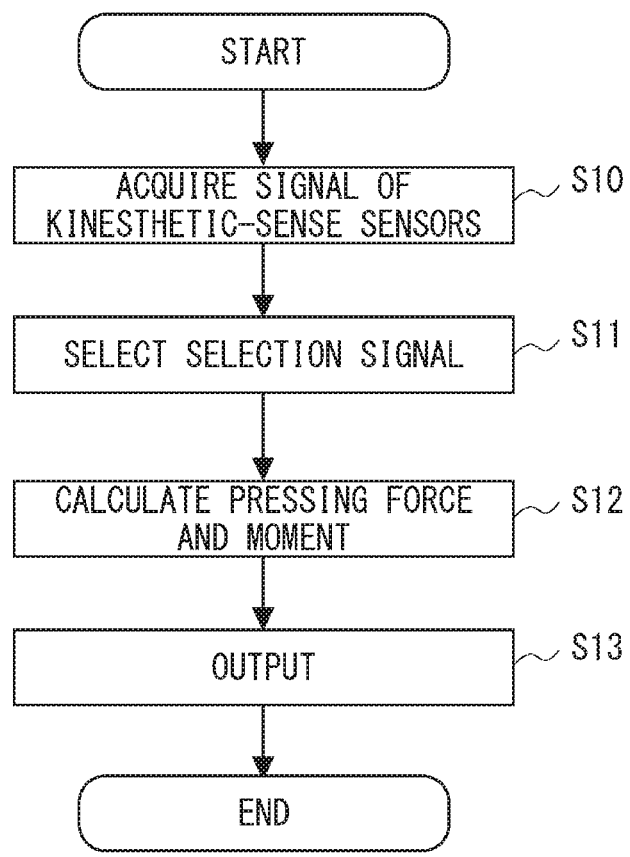
FIG. 9 is a flowchart showing processes performed by a sensor system.

Next, processes performed by the sensor system 10 are described with reference to FIG. 9. FIG. 9 is a flowchart showing processes performed by the sensor system. In particular, FIG. 9 shows processes performed by the control unit 15 of the sensor system 10.

Firstly, when the robot hand 1 grasps an object, the control unit 15 acquires signals (S1x, S1y, S1z) to (S8x, S8y, S8z) corresponding to pressing forces (f1x, f1y, f1z) to (f8x, f8y, F8z) in the three axial directions from the kinesthetic-sense sensors 11(1) to 11(8) (step S10).

Next, the control unit 15 selects calculation signals from the acquired signals of the kinesthetic-sense sensors 11 (step S11). More specifically, firstly, the selection unit 151 included in the control unit 15 acquires a threshold stored in the memory 16 and compares the value of the signal acquired from each kinesthetic-sense sensor with the acquired threshold. Then, the selection unit 151 determines whether or not the value of the signal acquired from each kinesthetic-sense sensor is larger the threshold. The selection unit 151 selects, from the signals acquired from the respective kinesthetic-sense sensors, signals that are not larger than the threshold as calculation signals used in the next step based on the determination result.

Note that in the memory 16, individual thresholds are stored for pressing forces in the three axial directions, respectively. Further, an individual threshold is also stored for a moment around the axis orthogonal to the reference plane is stored. Further, signals stored in the memory 16 are set for each kinesthetic-sense sensor. For example, among the plurality of kinesthetic-sense sensors shown in FIG. 2, values set for thresholds for the kinesthetic-sense sensors 11(1), 11(4), 11(5) and 11(8) disposed on the projection parts 12 are different from values set for thresholds for the kinesthetic-sense sensors 11(2), 11(3), 11(6) and 11(7) disposed on the reference plane 91A.

Next, the control unit 15 calculates each of the pressing forces in three axial directions and the moment around the axis orthogonal to the reference plane based on the selected calculation signals (step S12). More specifically, the arithmetic unit 152 included in the control unit 15 calculates each of the pressing forces in three axial directions and the moment around the axis orthogonal to the reference plane based on the calculation signals selected by the selection unit 151. The control unit 15 supplies the calculation result to the output unit 17.

Next, the output unit 17 outputs the calculation result received from the control unit 15 to the outside of the sensor system 10 (step S13).

Figure 10:
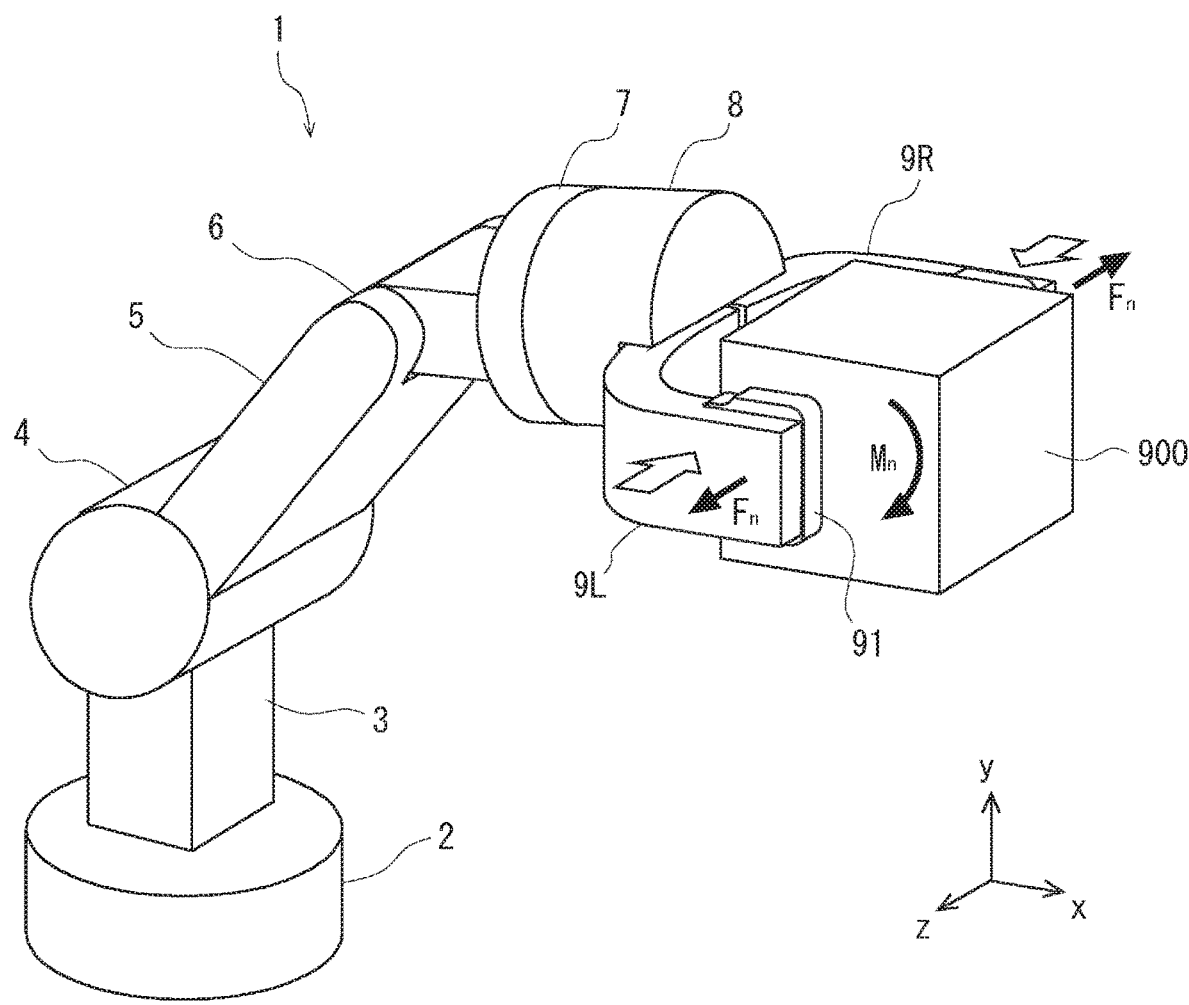
FIG. 10 is a perspective view of an external appearance showing a state in which a robot hand is grasping an object.

Next, specific examples of the processes in the above-described steps S11 and S12 as well as their details are described hereinafter. FIG. 10 is a perspective view of an external appearance showing a state in which a robot hand is holding (i.e., grasping) an object. In FIG. 10, the robot hand 1 is holding a cubic object 900. In the example shown in FIG. 10, the robot hand 1 is receiving a reaction force Fn in the z-axial direction in which the robot hand 1 is holding the object 900. Further, since the center of gravity of the object 900 is located on the x-axis positive side relative to the area where the grasping part 91 is holding the object 900, the grasping part 91 is receiving a moment Mn around the z-axis. In such a situation, the robot hand 1 calculates a pressing force Fn in the z-axial direction and the moment Mn around the z-axis, received from the object 900.

Figure 11:
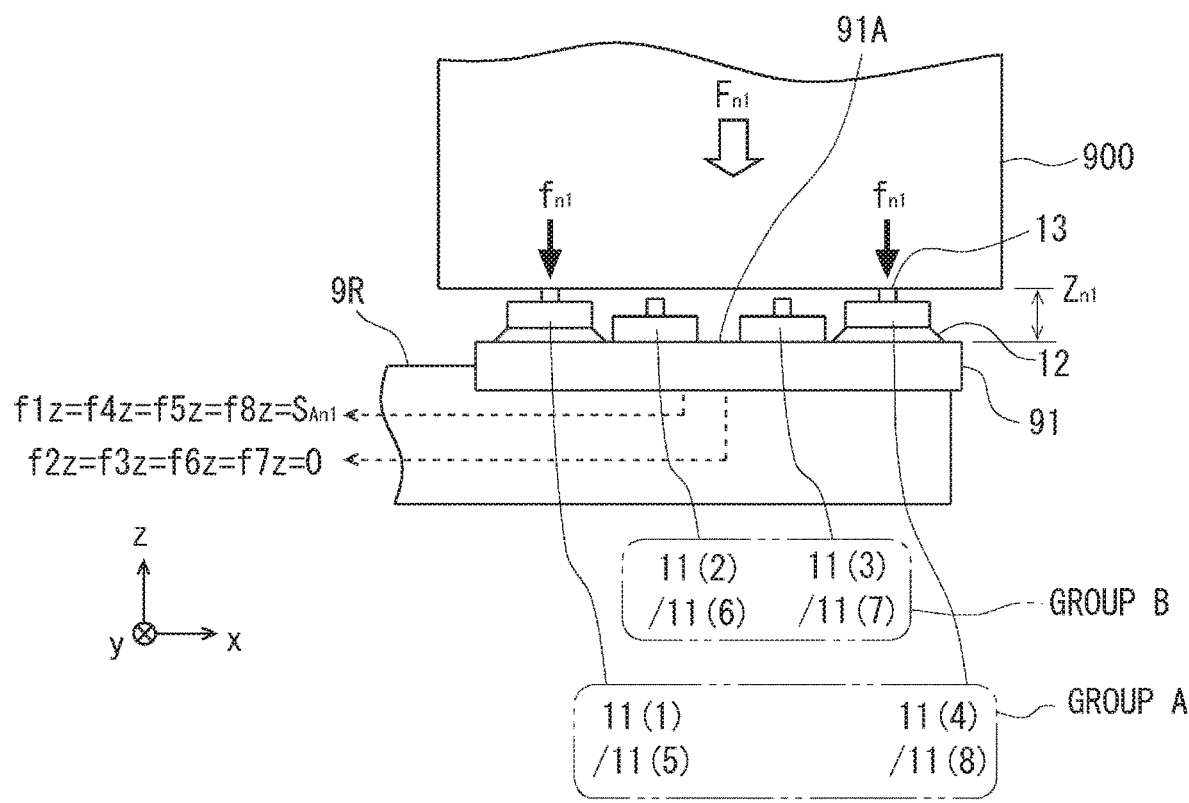
FIG. 11 shows an example of a state in which a pressing force in a z-axial direction is being applied to a first finger part.

FIG. 11 shows an example of a state in which a pressing force in the z-axial direction is being applied to the first finger part 9R. Note that, since the kinesthetic-sense sensor 11(1) is located in the same place as the kinesthetic-sense sensor 11(5) on the xz-plane shown in FIG. 11, a symbol indicating the kinesthetic-sense sensor 11(1) is also shown. Similarly, symbols of the kinesthetic-sense sensors 11(2) to 11(4) are also shown next to symbols of the respective kinesthetic-sense sensors located in the same places on the xz-plane. Further, for the sake of explanation, a group of four kinesthetic-sense sensors disposed on the projection parts 12 is referred to as a group A. Similarly, a group of four kinesthetic-sense sensors disposed on the reference plane 91A is referred to as a group B.

In FIG. 11, the object 900 is in contact with the kinesthetic-sense sensors of the group A with a pressing force $F_{n1}$. A divided force $f_{n1}$ is being applied to each of the kinesthetic-sense sensors of the group A. A distance $Z_{n1}$ between the object 900 and the reference plane 91A is larger than the height $Z_B$ and smaller than the height $Z_A$. Therefore, the object 900 is not in contact with the kinesthetic-sense sensors of the group B.

In such a state, the selection unit 151 acquires signals (f1z to f8z) corresponding to the pressing forces in the z-axial direction from the respective kinesthetic-sense sensors. In the example shown in FIG. 11, each of the kinesthetic-sense sensors of the group A outputs a signal $S_{An1}$ as an output corresponding to the divided force $f_{n1}$. Note that in this state, the outputs of the kinesthetic-sense sensors of the group B are zero.

Figure 12:
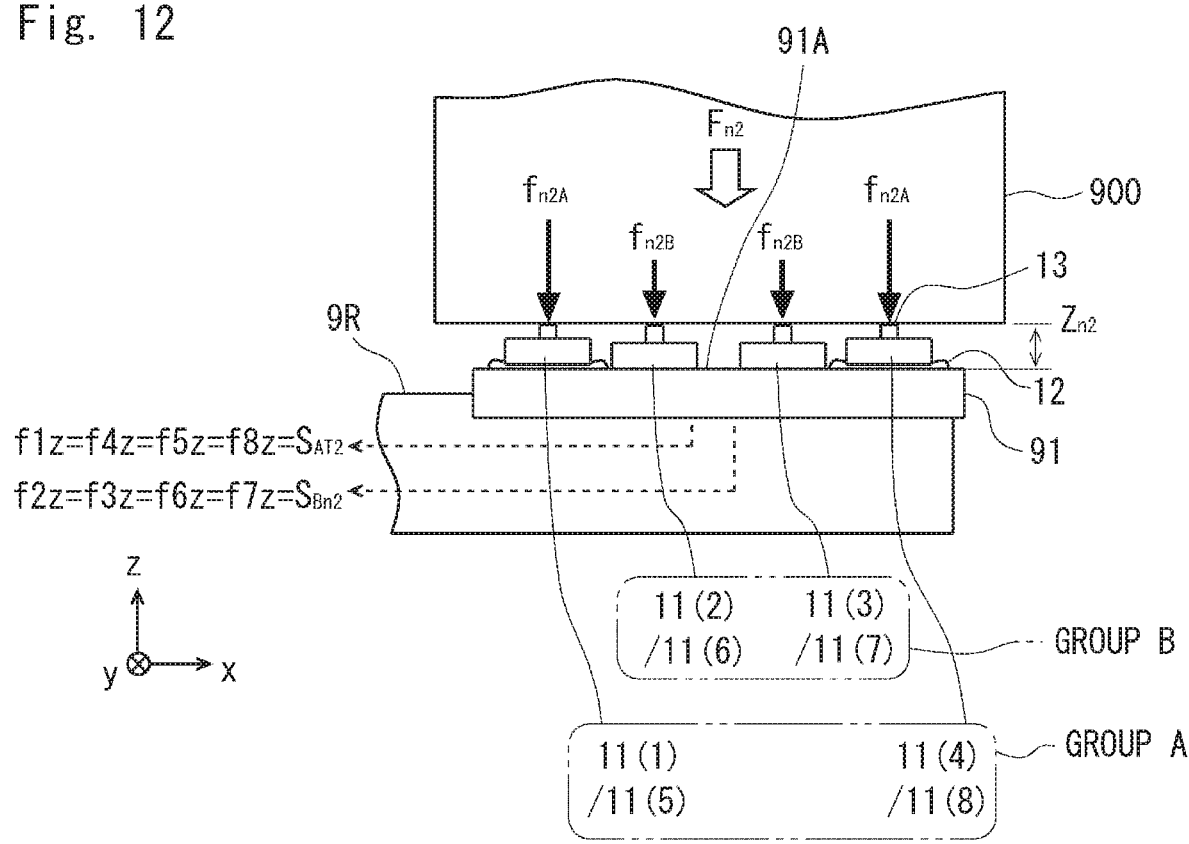
FIG. 12 shows another example of a state in which a pressing force in the z-axial direction is being applied to the first finger part.

Next, another example in which a pressing force in the z-axial direction is being applied to the first finger part 9R is described with reference to FIG. 12. FIG. 12 shows another example of a state in which a pressing force in the z-axial direction is being applied to the first finger part 9R.

In FIG. 12, an object 900 is in contact with the kinesthetic-sense sensors of the groups A and B with a pressing force $F_{n2}$. A divided force $f_{n2A}$ is being applied to each of the kinesthetic-sense sensors of the group A. A divided force $f_{n2B}$ is being applied to each of the kinesthetic-sense sensors of the group B. A distance $Z_{n2}$ between the object 900 and the reference plane 91A is smaller than the height $Z_B$. The object 900 is in contact with the kinesthetic-sense sensors of the groups A and B. Regarding the kinesthetic-sense sensors of the group A, the projection parts 12 are in a compressed state.

In such a state, the selection unit 151 acquires signals (f1z to f8z) corresponding to the pressing forces in the z-axial direction from the respective kinesthetic-sense sensors. In the example shown in FIG. 12, each of the kinesthetic-sense sensors of the group A outputs a signal $S_{AT2}$ as an output corresponding to the divided force $f_{n2A}$. Each of the kinesthetic-sense sensors of the group B outputs a signal $S_{Bn2}$ as an output corresponding to the divided force $f_{n2B}$.

As shown in FIGS. 11 and 12, each kinesthetic-sense sensor outputs a signal corresponding to the pressing force received from the object 900. Then, the selection unit 151 determines whether or not the signal output from each kinesthetic-sense sensor is larger than a predetermined threshold.

Figure 13:
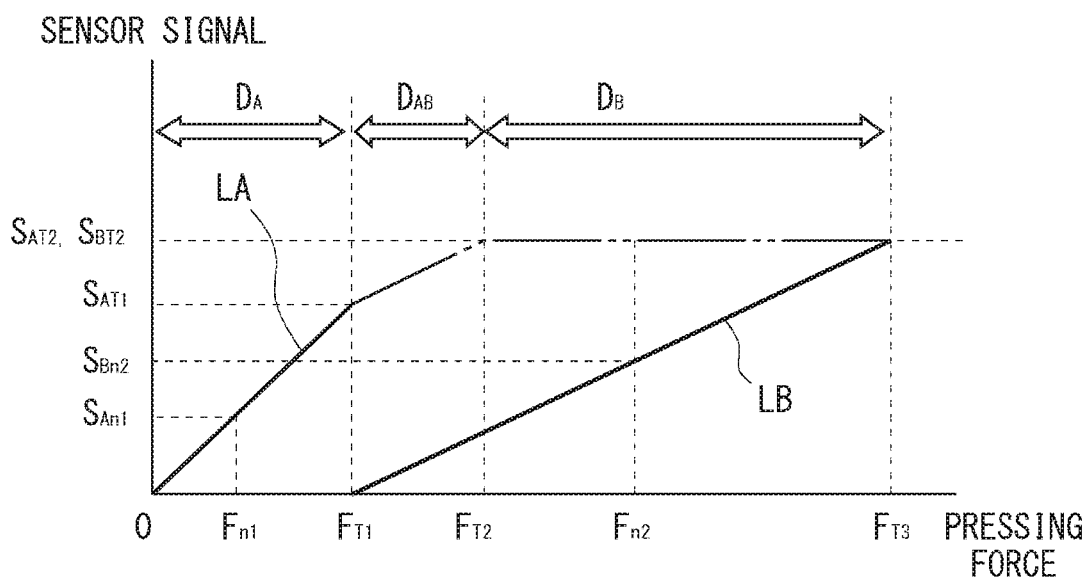
FIG. 13 is a graph showing a relation between signals of kinesthetic-sense sensors and pressing forces in the z-axial direction.

Next, a principle based on which the selection unit 151 selects calculation signals and the arithmetic unit 152 calculates pressing forces is described with reference to FIG. 13. FIG. 13 is a graph showing a relation between signals from kinesthetic-sense sensors and pressing forces in the z-axial direction. In the graph, a vertical axis indicates signals from kinesthetic-sense sensors corresponding to the z-axial direction, and a horizontal axis indicates pressing forces in the z-axial direction applied by an object 900. A polygonal line LA in FIG. 13 indicates outputs from the kinesthetic-sense sensors of the group A. A straight line LB in FIG. 13 indicates outputs from the kinesthetic-sense sensors of the group B.

Processes that are performed by the control unit 15 on the assumption that a pressing force increases from zero are described hereinafter. In a period in which the pressing force increases from zero to $F_{T1}$, an object 900 first comes into contact with the kinesthetic-sense sensors of the group A disposed on the projection parts 12. As a result, the kinesthetic-sense sensors of the group A output a signal that increases from zero to $S_{AT1}$ in proportion to the pressing force. During this period, the kinesthetic-sense sensors are gradually pushed in the z-axial negative direction by the object 900. That is, in the kinesthetic-sense sensors of the group A, their contact parts 13 are pushed as described above with reference to FIG. 6A, or the contact parts 13 are pushed and the projection parts 12 are compressed at the same time.

When the pressing force reaches Fri, the object 900 also comes into contact with the kinesthetic-sense sensors of the group B. Therefore, when the pressing force is equal to or larger than Fri, the signal of the kinesthetic-sense sensors of the group B is larger than zero. Note that the inclination (i.e., the change) of the output of the group B is gentler than that of the output of the group A. This is because when the kinesthetic-sense sensors of the group B are pressed, the kinesthetic-sense sensors of the group A are also pressed at the same time.

The inclination of the polygonal line LA is slightly reduced at $F_{T1}$ and the polygonal line LA extends to $F_{T2}$ with the reduced inclination. This is because the object 900 is also in contact with the kinesthetic-sense sensors of the group B at and after $F_{T1}$ as described above. The group A outputs the signal $S_{AT2}$ at the pressing force $F_{T2}$.

At and after $F_{T2}$, the output of the group A is maintained at $S_{AT2}$. This is because the displacement of the contact parts 13 of the kinesthetic-sense sensors has reached a predetermined distance. Therefore, after that, even when the pressing force increases, the signal output from the group A does not change. When the pressing force is equal to or larger than $F_{T2}$, the projection parts 12 are compressed to such an extent that the kinesthetic-sense sensors of the group A do not disturb the external force from the object 900.

When the pressing force reaches $F_{T3}$, the displacement of the contact parts 13 of the kinesthetic-sense sensors of the group B reaches a predetermined distance. That is, this means that all the kinesthetic-sense sensors 11 have reached the upper limit of the detection range for the pressing force in the z-axial direction in the sensor system 10.

Regarding the above-described range of the pressing force from zero to $F_{T3}$, in the range of the pressing force from zero to $F_{T1}$, the control unit 15 calculates the pressing force based on the output of the group A. That is, in the range $D_A$ of the pressing force from zero to $F_{T1}$, the selection unit 151 selects the output of the kinesthetic-sense sensors of the group A as calculation signals. Then, the arithmetic unit 152 obtains the pressing force by adding up the outputs of the kinesthetic-sense sensors of the selected group A.

Further, in the range $D_{AB}$ of the pressing force from $F^{T1}$ to $F_{T2}$, the control unit 15 calculates the pressing force based on the outputs of the groups A and B. That is, when the signal of the group B starts to be output, the selection unit 151 selects the signals of the groups A and B as calculation signals until immediately before the signal of the group A reaches the upper limit $S_{AT2}$. Then, the arithmetic unit 152 obtains the pressing force by adding up the outputs of the kinesthetic-sense sensors of the groups A and B, which are the selected calculation signals.

In the range $D_B$ of the pressing force from $F_{T2}$ to $F_{T3}$, the control unit 15 calculates the pressing force based on the output of the group B. That is, when the signal of the group A reaches $S_{AT2}$, which is the upper limit, the selection unit 151 selects the signal of the group B as the calculation signals. Then, the arithmetic unit 152 adds up the outputs of the kinesthetic-sense sensors of the group B, which are the selected calculation signals. Further, the arithmetic unit 152 estimates and adds up the pressing force received by the kinesthetic-sense sensors of the group A according to the output of the kinesthetic-sense sensors of the group B.

The estimation of the pressing force received by the kinesthetic-sense sensors of the group A, performed by the arithmetic unit 152 is described hereinafter. When the groups A and B are displaced in proportion to a certain linear function with respect to the pressing force, a pressing force $f_A$ received by the kinesthetic-sense sensors of the group A is expressed by the below-shown Expression (2).

[Expression 2]

$$f_A = k_A \cdot z \tag{2}$$

In the expression, $k_A$ is a spring coefficient generated by a combination of the kinesthetic-sense sensors of the group A and their projection parts 12, and z is a displacement by which the kinesthetic-sense sensors are pushed from the height $Z_A$ in the z-axis negative direction.

Meanwhile, a displacement z of the contact parts 13 of the kinesthetic-sense sensors of the group B can be obtained by the below-shown Expression (3).

[Expression 3]

$$z = \frac{S_B(z)}{\beta} + z1 \tag{3}$$

In the expression, $S_B(z)$ is a signal output by the kinesthetic-sense sensors at the displacement z, and β is an eigenvalue of the kinesthetic-sense sensors of the group B. Further, z1 is a difference between the groups A and B described above with reference to FIG. 3 or a height $(Z_A - Z_B)$ of the projection parts 12.

When the kinesthetic-sense sensors of the group B output signals, the displacement z can be obtained from Expression (3). Then, the pressing force $f_A$ received by the kinesthetic-sense sensors of the group A can be calculated by substituting the displacement z obtained by Expression (3) into Expression (2). The arithmetic unit 152 can calculate the pressing force received by the kinesthetic-sense sensors of the group A from the signal of the kinesthetic-sense sensors of the group B by performing the above-described calculation. Further, since the signal of the kinesthetic-sense sensors of the group B is (i.e., represents) the pressing force received by the group B, the pressing force in the z-axial direction received from the object 900 can be calculated by adding up them.

The pressing force $F_{n1}$ corresponding to the example shown in FIG. 11 is plotted in the graph shown in FIG. 13. The signal of the kinesthetic-sense sensors of the group A at the pressing force $F_{n1}$ is $S_{An1}$. Further, the signal of the kinesthetic-sense sensors of the group B at the pressing force $F_{n1}$ is zero. Therefore, in this case, the selection unit 151 selects the signal of the kinesthetic-sense sensors of the group A as calculation signals.

The pressing force $F_{n2}$ corresponding to the thick arrow shown in FIG. 12 is also plotted in the graph shown in FIG. 13. The signal of the kinesthetic-sense sensors of the group A at the pressing force $F_{n2}$ is $S_{AT2}$, which is the upper-limit value. Further, the signal of the kinesthetic-sense sensors of the group B at the pressing force $F_{n2}$ is $S_{Bn2}$. Therefore, in this case, the selection unit 151 selects the signal of the kinesthetic-sense sensors of the group B as calculation signals.

As described above, in the sensor system 10, a plurality of kinesthetic-sense sensors of the same type are arranged in each of the reference plane and the projection parts. Further, a pressing force is calculated by using appropriately selected signals. In this way, the dynamic range in the direction perpendicular to the reference plane can be expanded as compared to the case where all the kinesthetic-sense sensors are arranged on the same plane.

Note that the inclination of the polygonal line LB of the signal output from the kinesthetic-sense sensors 11 of the group B is gentler (i.e., smaller) than that of the polygonal line LA of the signal output from the kinesthetic-sense sensors 11 of the group A. That is, the range (i.e., the amount of change) of the signal output by the kinesthetic-sense sensors 11 of the group B with respect to the change of the pressing force is smaller than that of the kinesthetic-sense sensors 11 of the group A. This means that the resolution of the output with respect to the pressing force is slightly reduced. However, the resolution is higher than that in the case where the range up to the pressing force $F_{T3}$ is covered by using only one kinesthetic-sense sensor 11. That is, by adopting the configuration of the embodiment, it is possible to expand the dynamic range of the sensor system 10 while preventing the decrease in the resolution.

Figure 14:
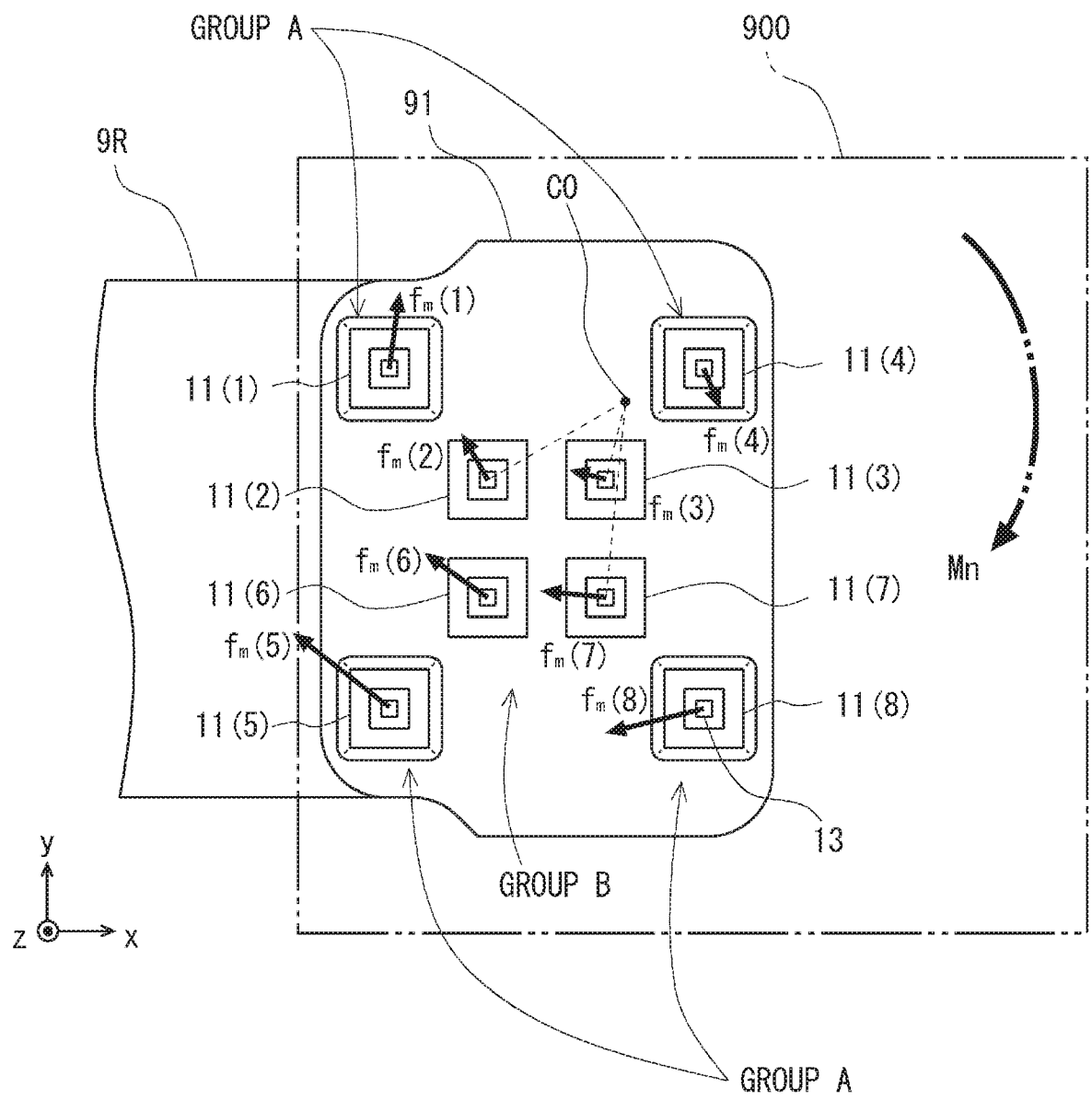
FIG. 14 is a diagram for explaining a moment applied to kinesthetic-sense sensors.

Next, a process for calculating a moment around the z-axis is described with reference to FIG. 14. FIG. 14 is a diagram for explaining a moment applied to kinesthetic-sense sensors. In FIG. 14, the kinesthetic-sense sensors disposed in the grasping part 91 receive a moment around the z-axis centered at a point C0 from an object 900. The kinesthetic-sense sensors 11 detect pressing forces (f1x to f8x) in the x-axial direction and pressing forces (f1y to f8y) in the y-axial direction. Each of the kinesthetic-sense sensors 11 can obtain its force vector applied on the xy-plane based on a resultant force of the pressing forces in the x- and y-axial directions. The force vectors of the kinesthetic-sense sensors 11 are indicated by fm (1) to fm (8), respectively, shown in FIG. 14. A moment applied to each kinesthetic-sense sensor 11 can be calculated by multiplying a respective one of the force vectors fm (1) to fm (8) by a distance from the point C0, which is the center of the moment, to that kinesthetic-sense sensor 11.

However, when a force larger than a predetermined force is applied to the kinesthetic-sense sensor, there is a possibility that an accurate force moment could not be output. For example, when a large force is applied to the above-described kinesthetic-sense sensors 11 in the z-axial negative direction, their contact parts 13 cannot be easily moved on the xy-plane. Further, even when a large force is not applied to the kinesthetic-sense sensors 11 in the z-axial direction, if a force larger than a predetermined force is applied in the x- or y-axial direction, a force vector cannot be accurately calculated. Therefore, in the sensor system 10 according to the embodiment, the selection unit 151 selects some of the signals acquired from the kinesthetic-sense sensors 11 and calculates the moment based on the selected calculation signals.

As described above with reference to FIG. 9, firstly, the control unit 15 acquires a signal from each of the kinesthetic-sense sensors 11 (step S10). Next, the selection unit of the control unit 15 selects calculation signals from the acquired signals (step S11). The grasping part 91 shown in FIG. 14 is identical to the example shown in FIGS. 10 and 12. That is, among the eight kinesthetic-sense sensors 11, forces larger than a predetermined value are being applied to the kinesthetic-sense sensors of the group A in the z-axial direction. Further, among the four kinesthetic-sense sensors of the group B, a pressing force that is being applied to the kinesthetic-sense sensor 11(6) located farthest from the point C0, which is the center of the moment, in the x-axial direction is larger than a predetermined value. Therefore, the selection unit 151 excludes the four kinesthetic-sense sensors of the group A and the kinesthetic-sense sensor 11(6), and selects signals (fm(2), fm(3) and fm(7)) acquired from the kinesthetic-sense sensors 11(2), 11(3) and 11(7) as calculation signals.

Next, the arithmetic unit 152 obtains the point C0, which is the center of the moment, from the calculation signals selected by the selection unit 151. Specifically, for example, the arithmetic unit 152 calculates force vectors of the kinesthetic-sense sensors 11(2), 11(3) and 11(7), which are selected for the calculation signals, and obtains intersections of perpendiculars of these force vectors. When the three perpendiculars do not intersect at one point, a middle point of a plurality of intersections may be used as the center. The arithmetic unit 152 calculates a moment in each of the kinesthetic-sense sensors 11 by multiplying a distance from the point C0, which is obtained as described above, to that kinesthetic-sense sensor 11 by a force vector in that kinesthetic-sense sensor 11.

As described above, the sensor system 10 selects, as calculation signals, signals output by kinesthetic-sense sensors 11 that have output signals no larger than the predetermined threshold among the plurality of kinesthetic-sense sensors 11. In this way, it is possible to appropriately calculate the moment around the axis orthogonal to the reference plane. Further, by being equipped with the plurality of kinesthetic-sense sensors 11, the sensor system 10 can select signals having a higher resolution from the kinesthetic-sense sensors 11 that have output signals no larger than the predetermined threshold.

Note that after obtaining the point C0, which is the center, from the selected calculation signals, the arithmetic unit 152 may also calculate moments in kinesthetic-sense sensors 11 that have not been selected by using the point C0. In this way, it is possible to, after appropriately obtaining a rotation center of the moment, calculate the sum total of the overall moment applied to the grasping part.

Details of the embodiment have been described above. Note that although the projection parts 12 are compressible in the above-described example, the projection parts 12 may be rigid and incompressible. In such a case, when an object to be grasped is not flexible, the kinesthetic-sense sensors of the group A detect an external force. Further, when the object to be grasped is flexible and the object comes into contact with the kinesthetic-sense sensors of the group B, the kinesthetic-sense sensors of the group B can also detect the external force. Therefore, it is possible to determine whether the object to be grasped is hard or soft. Although the above-described grasping part 91 has four kinesthetic-sense sensors in the group A and four kinesthetic-sense sensors in the group B, the only requirement is that each group should have at least one kinesthetic-sense sensor.

Further, the grasping part 91 may have a plurality of types of projection parts having different heights. In this way, it is possible to further expand the dynamic range of the sensor system 10 in the axial direction orthogonal to the reference plane while reducing the decrease in its resolution.

Further, the control unit 15 and the memory 16 may perform signal processing for the kinesthetic-sense sensors 11 included in the second finger part 9L in addition to signal processing for those included in the first finger part 9R. Note that the second finger part 9L may be connected to another control unit and another memory.

The control unit 15, the memory 16, and the output unit 17 may not be included in the robot hand 1, and configured to receive signals of the kinesthetic-sense sensors 11 transmitted from the robot hand 1 and perform a predetermined outputting process based on the received signals of the kinesthetic-sense sensors 11. In this case, for example, the control unit 15, the memory 16, and the output unit 17 may be included in a part of a configuration of a computer.

<Method for Calibrating Sensor System>

Next, a method for calibrating a sensor system 10 in a robot hand 1 according to an embodiment is described. The sensor system 10 includes a plurality of kinesthetic-sense sensors 11. Therefore, it is desirable to perform a method in which a characteristic of each of three axial directions of each of them is easily calibrated and certain accuracy is secured.

Figure 15:
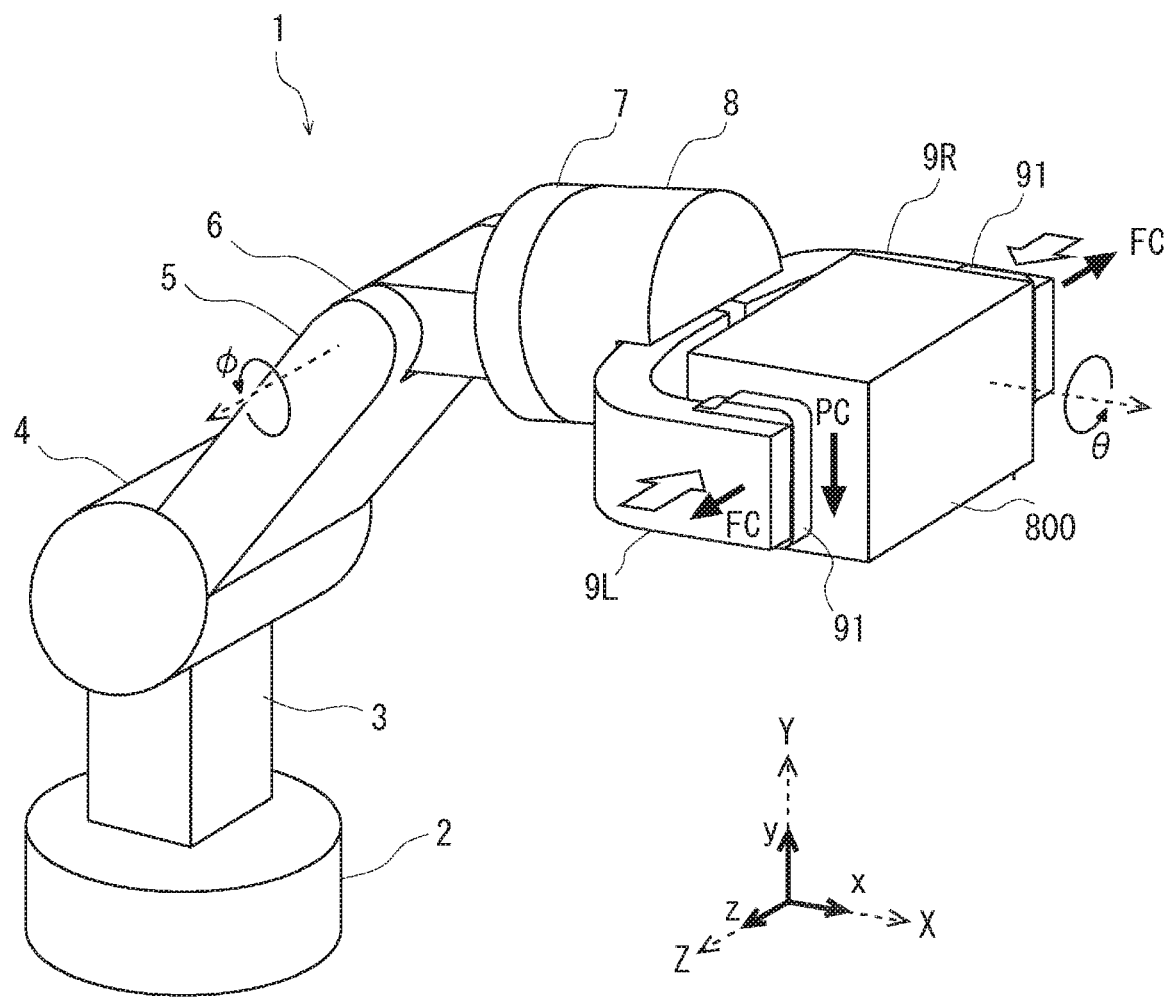
FIG. 15 is a perspective view of an external appearance showing a state of a robot hand in which calibration is performed for a sensor system.

FIG. 15 is a perspective view of an external appearance showing a state of a robot hand 1 in which calibration is performed for a sensor system 10. The robot hand 1 is holding (i.e., grasping) a reference object 800 with a predetermined force. The reference object 800 is a component having a quadrangular-prism shape. Further, the reference object 800 is made of a single material, so that its weight (i.e., its density) is uniform. The two surfaces of the reference object 800 and the grasping part 91 that come into contact with each other are parallel. The surface of the reference object 800, which comes into contact with the grasping part 91, may have a high friction coefficient so that the robot hand 1 can grasp the reference object 800 without requiring an excessive force. In the figure, the robot hand 1 is holding the reference object 800 along the z-axial direction. By grasping the reference object 800, the grasping part 91 receives a pressing force FC in the z-axial direction and receives a pressing force PC in the y-axis negative direction, which coincides with the gravitational direction.

Note that in FIG. 15, an xyz-coordinate system and an XYZ-coordinate system are shown in a superimposed manner. Note that the xyz-coordinate system is a local coordinate system that moves with the first finger part 9R. The XYZ-coordinate system is a global coordinate system.

Figure 16:
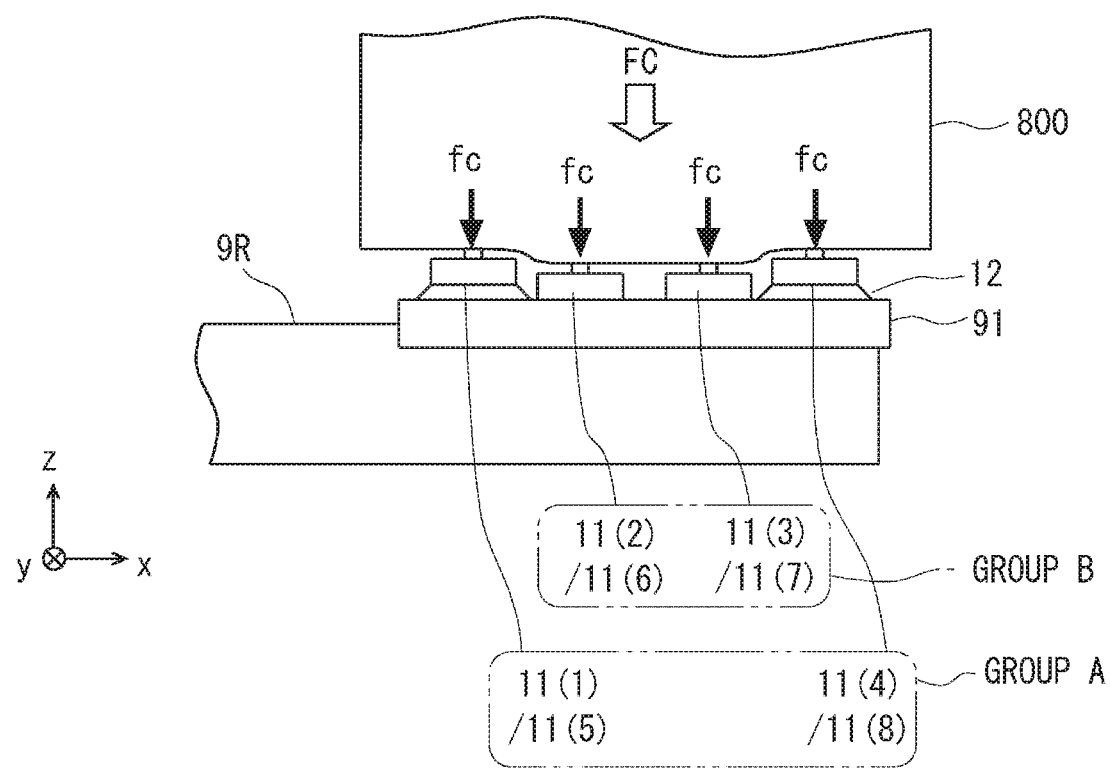
FIG. 16 is a diagram for explaining details of the first finger part.

The pressing forces received by the grasping part 91 are further described with reference to FIG. 16. FIG. 16 is a diagram for explaining details of the first finger part 9R. The grasping part 91 includes kinesthetic-sense sensors of the group A disposed on the projection parts 12 and kinesthetic-sense sensors of the group B disposed in the reference plane. The reference object 800 has a convex shape having the same height as that of the projection parts 12 in the central part. In this way, the reference object 800 can apply a constant divided force fc (i.e., the same divided force fc) to each of all the kinesthetic-sense sensors 11 included in the groups A and B. Similarly, the reference object 800 can apply a divided force pc of the pressing force PC to each of all the kinesthetic-sense sensors 11 in the y-axial negative direction.

FIG. 15 is referred to again. The robot hand 1 can change the posture of the reference object 800 by rotating the third joint 8. Note that the rotation angle of the third joint 8 is represented by θ. The posture shown in FIG. 15 corresponds to a state where θ is 0 degrees. Similarly, the robot hand 1 can change the posture of the reference object 800 by rotating the second joint 6. Note that the rotation angle of the second joint 6 is represented by φ. The posture shown in FIG. 15 corresponds to a state where φ is 0 degrees. The robot hand 1 changes pressing forces received by the kinesthetic-sense sensors 11 of the grasping part 91 by driving the second and third joints 6 and 8 and thereby changing the posture of the reference object 800. By doing so, the robot hand 1 calibrates the kinesthetic-sense sensors 11 for each of predetermined postures of the reference object 800.

Figure 17:
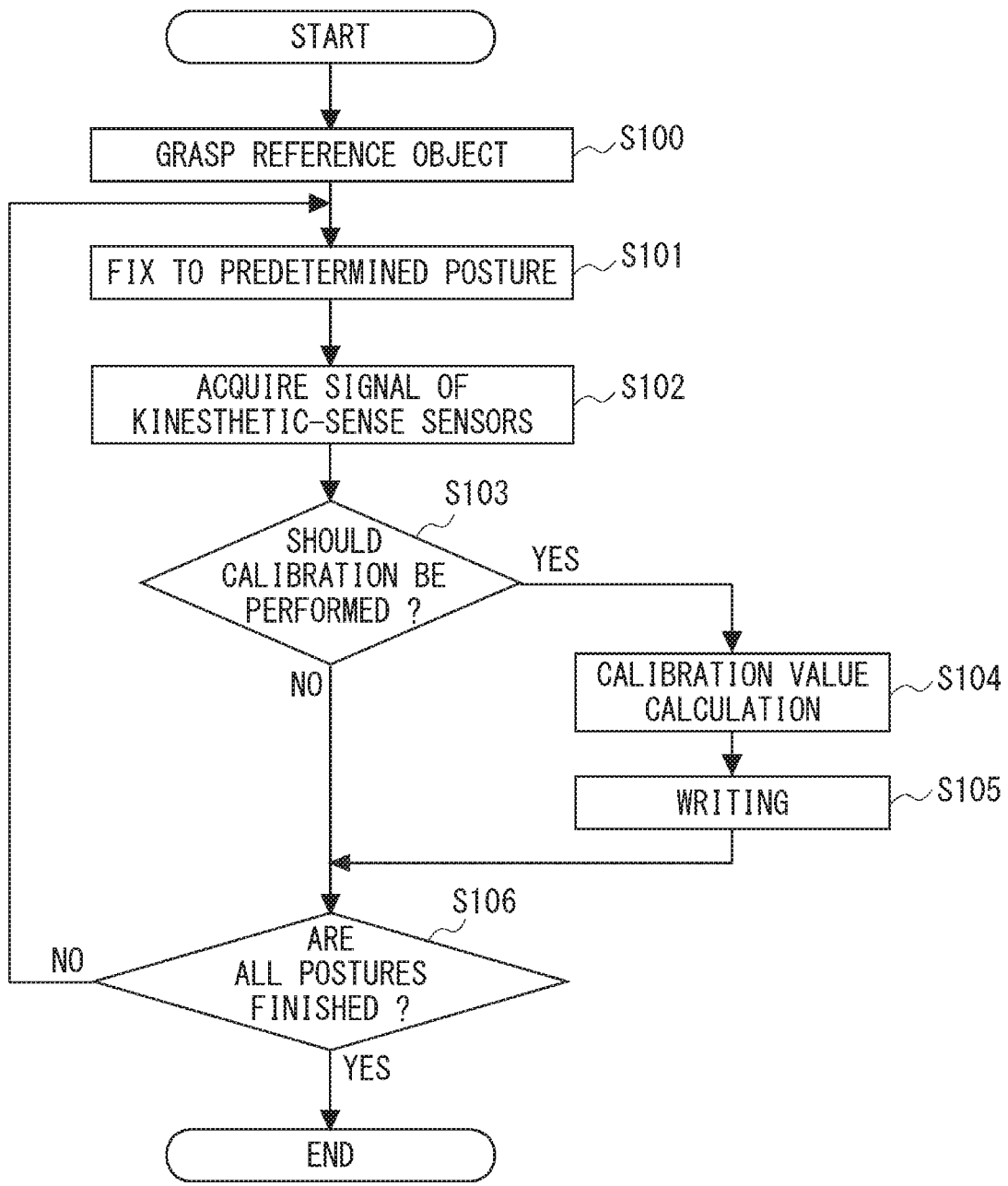
FIG. 17 is a flowchart of a calibration process performed by a sensor system.

Next, the calibration process for the sensor system 10 is further described with reference to FIGS. 17 to 19. FIG. 17 is a flowchart of the calibration process performed by the sensor system. Firstly, the robot hand 1 grasps a reference object 800 (step S100). Note that the robot hand 1 may have an arbitrary posture. However, the relative position between the reference object 800 and the grasping part 91 should be within a predetermined range so that no moment like the one shown in FIG. 10 occurs.

Next, the robot hand 1 is fixed in a predetermined posture by driving each joint (step S101). The predetermined posture is, for example, the posture shown in FIG. 15 in which φ and θ are both 0 degrees.

Next, the sensor system 10 acquires a signal from each kinesthetic-sense sensor 11 (step S102). In the posture shown in FIG. 15, a divided force pc is applied to the kinesthetic-sense sensors 11 in the y-axial direction and a divided force fc is applied to them in the z-axial direction. Further, the load in the x-axial direction is zero.

The sensor system 10 compares the acquired signals of the kinesthetic-sense sensors 11 with reference values, which are stored in advance, and thereby determines whether or not to calibrate the output of the kinesthetic-sense sensors 11 (step S103). When the difference between the signal output from the kinesthetic-sense sensor 11 and the reference value is smaller than the predetermined range (step S103: No), the sensor system 10 proceeds to a step S106. On the other hand, when the difference between the signal output by the kinesthetic-sense sensor 11 and the reference value is not smaller than the predetermined range (step S103: Yes), the sensor system 10 calculates a calibration value for performing calibration for a difference between the signal of the kinesthetic-sense sensor 11 and the reference value (step S104). Further, the sensor system 10 writes the calculated calibration value into a predetermined register or a memory (step S105).

Next, the sensor system 10 determines whether or not the processes for all the postures have been completed (step S106). When the processes for all the postures have not been finished, the process returns to the step S101 and the robot hand 1 is changed to and fixed in a posture for which the process has not been completed yet among the predefined postures.

Figure 18:
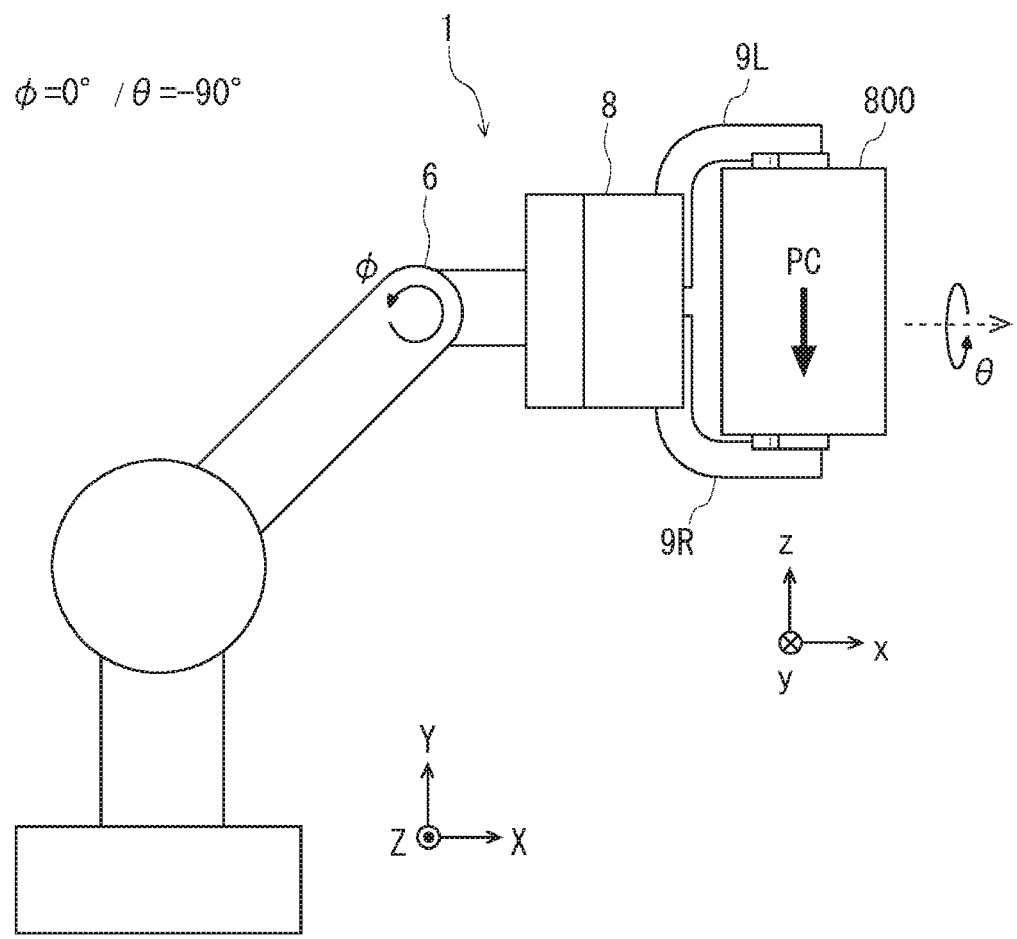
FIG. 18 is a diagram for explaining a robot hand that performs a calibration process.

FIG. 18 is a diagram for explaining a robot hand that performs a calibration process. FIG. 18 shows a state in which θ is set to −90 degrees by rotating the third joint 8. In this state, divided forces of a pressing force PC are applied to the kinesthetic-sense sensors 11 of the first finger part 9R in the z-axial direction, and the loads in the x- and y-axial directions are zero. The sensor system 10 acquires signals from the kinesthetic-sense sensors 11 again in this posture (step S102) and performs the calibration process up to the step S106.

Figure 19:
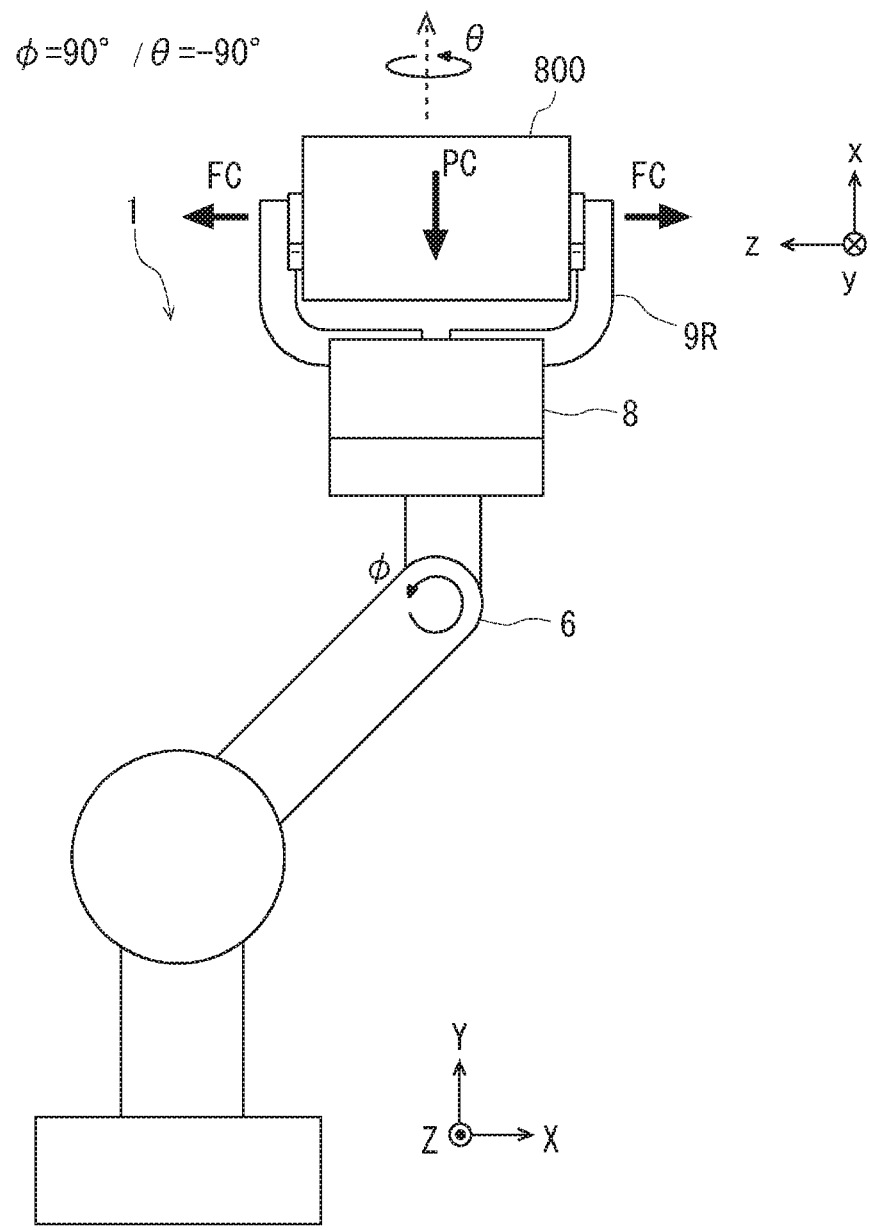
FIG. 19 is a diagram for explaining a robot hand that performs a calibration process.

Next, the sensor system 10 changes the posture of the robot hand 1 to a posture shown in FIG. 19 and performs the calibration process. FIG. 19 shows a state in which φ is 90 degrees and θ is −90 degrees. In this state, divided forces of a pressing force PC are applied to the kinesthetic-sense sensors 11 of the first finger part 9R in the x-axis negative direction and divided forces of a pressing force FC are applied to them in the z-axis negative direction. Further, the load in the y-axial direction is zero. The sensor system 10 acquires signals from the kinesthetic-sense sensors 11 again in this posture (step S102) and performs the calibration process up to the step S106.

FIG. 17 is referred to again. The robot hand 1 performs the calibration process in the predetermined posture as described above. Further, in the step S106, when it is determined that the processes for all the postures are finished (step S106: Yes), the process is finished.

The calibration process for the robot hand 1 has been described above. It should be noted that the sensor system 10 may compare the acquired signal of the kinesthetic-sense sensors 11 with an average value of signals acquired from the kinesthetic-sense sensors 11, instead of comparing it with the above-described reference value. Further, the average value may be a weighted average or a moving average.

Modified Example 1 of Embodiment

Figure 20:
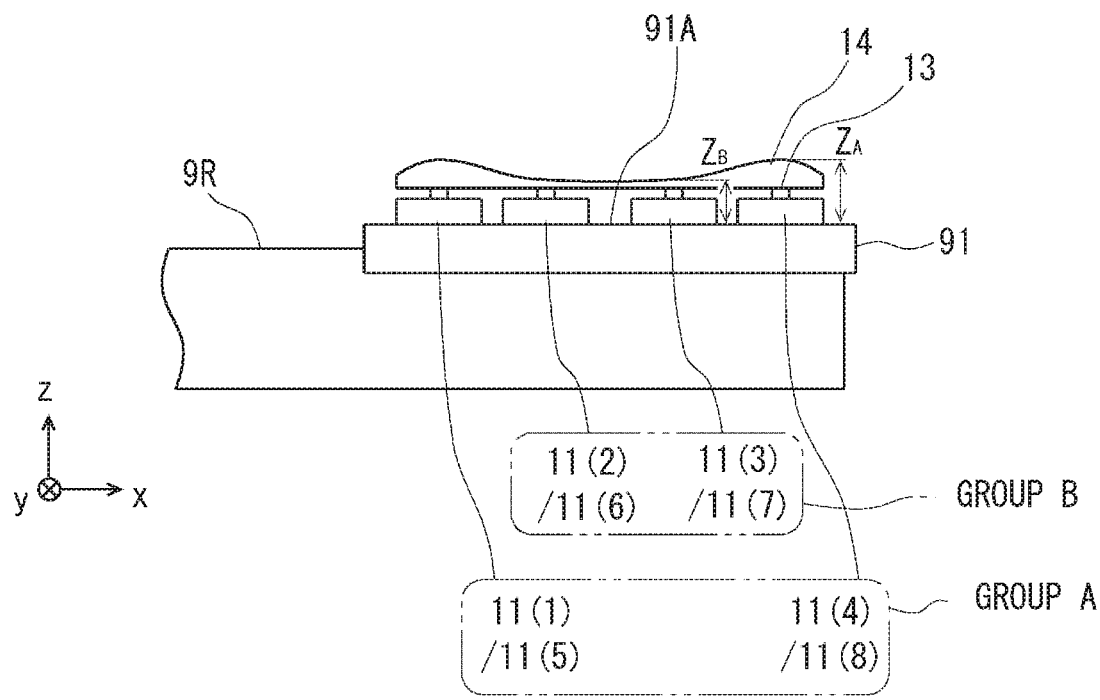
FIG. 20 is a diagram for explaining a modified example 1 of an embodiment.

Next, a modified example 1 of the embodiment is described. FIG. 20 is a diagram for explaining the modified example 1 of the embodiment. In the modified example 1 of the embodiment, no projection part 12 is provided on the reference plane 91A and all of the eight kinesthetic-sense sensors 11 are disposed on the reference plane 91A. A contact member 14, which comes into contact with an object to be grasped, is provided on surfaces on the z-axis positive side of the contact parts 13.

The contact member 14 is a flexible sheet-like member and is disposed so as to cover the contact parts 13 of all of the eight kinesthetic-sense sensors 11. Further, the contact member 14 has such a shape that its thickness in the z-axial direction is not uniform. More specifically, the thickness of the part of the contact member 14 corresponding to the contact parts 13 of the kinesthetic-sense sensors 11 of the group A is uniform and a height from the reference plane 91A to the top surface of this part is $Z_A$. Meanwhile, the thickness of the part of the contact member 14 corresponding to the contact parts 13 of the kinesthetic-sense sensors 11 of the group B is uniform and a height from the reference plane 91A to the top surface of this part is $Z_B$. Further, the height $Z_A$ is larger than the height $Z_B$.

By the above-described configuration, in the robot hand according to the modified example 1 of the embodiment, a plurality of kinesthetic-sense sensors 11 are all disposed on the grasping parts 91 and one component (e.g., the contact member 14) is disposed for the contact parts 13 of the plurality of the disposed kinesthetic-sense sensors 11. Therefore, the robot hand can be easily assembled. Further, since the setting of the groups A and B can be made by the contact member 14, it is flexibly adapted.

Modified Example 2 of Embodiment

Figure 21:
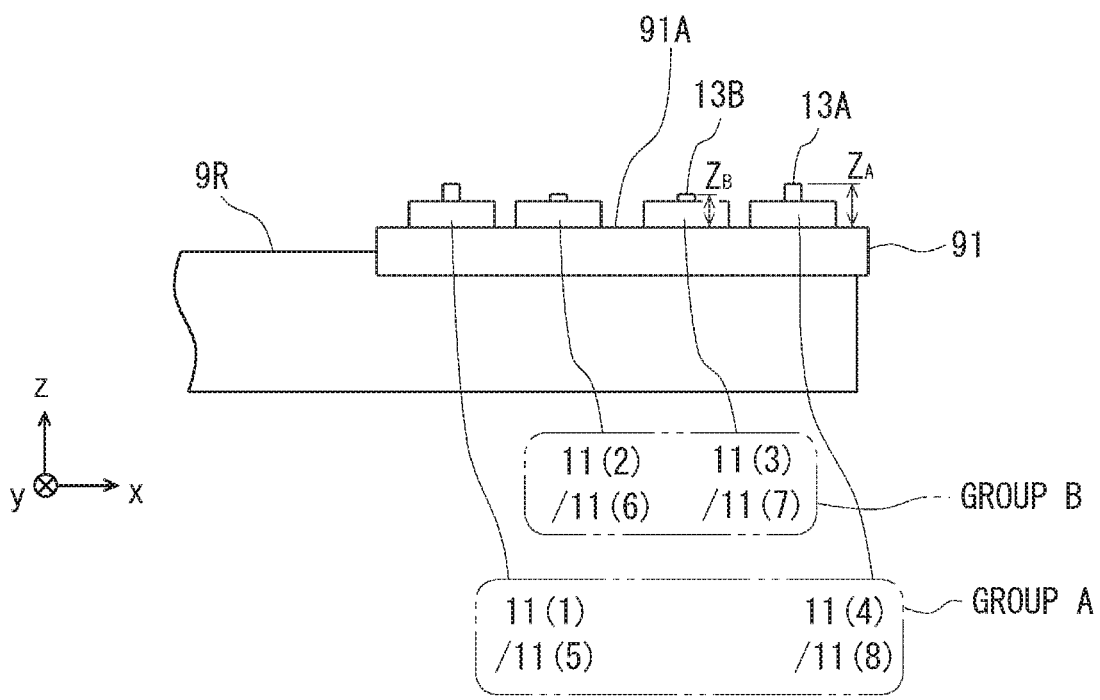
FIG. 21 is a diagram for explaining a modified example 2 of the embodiment.

Next, a modified example 2 of the embodiment is described with reference to FIG. 21. FIG. 21 is a diagram for explaining the modified example 2 of the embodiment. The modified example 2 of the embodiment differs from the above-described robot hand because it includes two types of contact parts, instead of including the projection parts 12 or the contact member 14.

In the robot hand according to the modified example 2 of the embodiment, the kinesthetic-sense sensors 11 of the group A include contact parts 13A whose height from the reference plane 91A in the z-axial direction is $Z_A$. Further, the kinesthetic-sense sensors 11 of the group B include contact parts 13B whose height from the reference plane 91A in the z-axial direction is $Z_B$. By the above-described configuration, the robot hand according to the modified example 2 of the embodiment can be constructed with a small number of components.

Modified Example 3 of Embodiment

Figure 22:
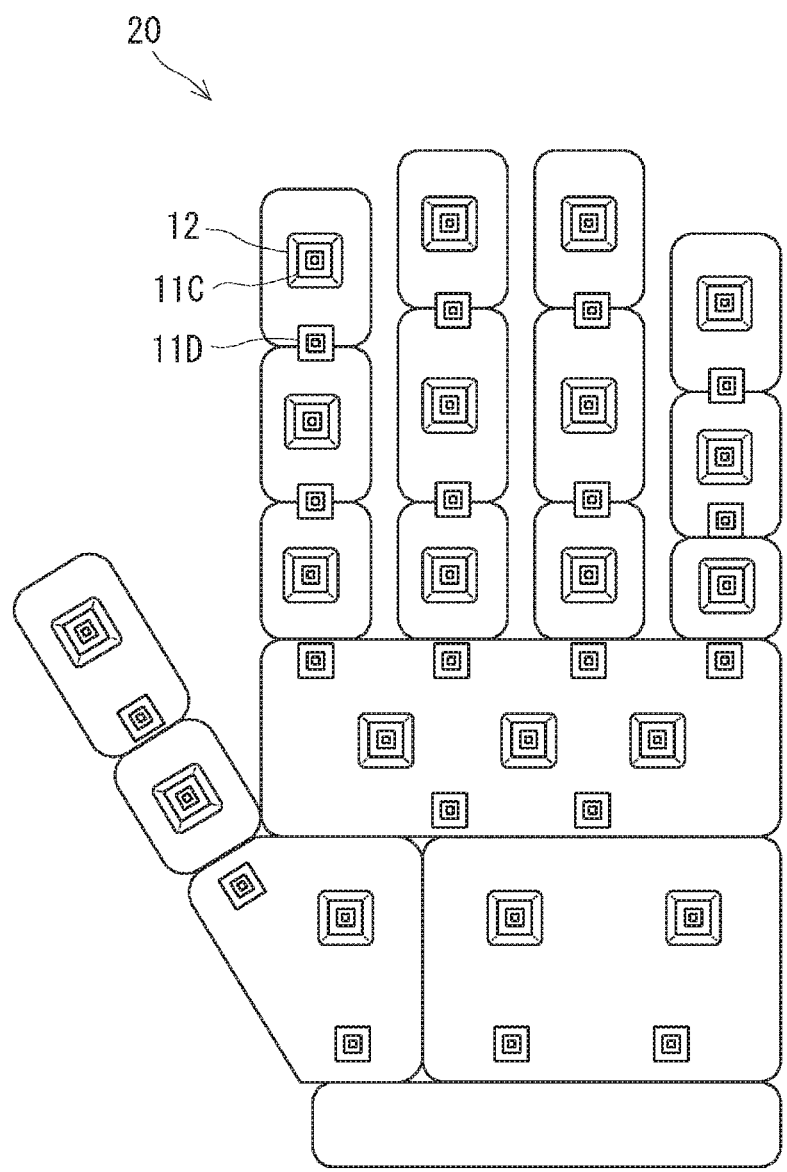
FIG. 22 is a diagram for explaining a modified example 3 of the embodiment.

Next, a modified example 3 of the embodiment is described with reference to FIG. 22. FIG. 22 is a diagram for explaining the modified example 3 of the embodiment. The modified example 3 of the embodiment differs from the above-described robot hand according to the embodiment because the sensor system 10 is applied to a five-fingered robot hand.

In the five-fingered robot hand 20, a plurality of projection parts 12 are arranged on a plurality of surfaces which come into contact with an object. Further, kinesthetic-sense sensors 11C are disposed on respective projection parts 12. Further, a plurality of kinesthetic-sense sensors 11D are disposed on respective surfaces (i.e., respective parts of the surface) of the five-fingered robot hand 20. By the above-described configuration, the robot hand 20 according to the modified example 3 of the embodiment can appropriately detect a pressing force for each of the plurality of surfaces which comes into contact with an object. Further, the robot hand 20 according to the modified example 3 of the embodiment can appropriately calculate a moment by selecting kinesthetic-sense sensors 11 that do not exceed a predetermined threshold from those disposed on the plurality of surfaces which comes into contact with an object.

Modified Example 4 of Embodiment

Next, a modified example 4 of the embodiment is described with reference to FIG. 23. FIG. 23 is a diagram for explaining the modified example 4 of the embodiment. The modified example 4 of the embodiment differs from the five-fingered robot hand 20 according to the modified example 3 of the embodiment because its kinesthetic-sense sensors mounted on the five-fingered robot hand are formed as unit sensors.

In the five-fingered robot hand 20, a plurality of sensor units 21 are provided on a plurality of surfaces which come into contact with an object. In each of the sensor units 21, two projection parts 12 are provided on a substrate 22 and two kinesthetic-sense sensors 11C are provided on the respective projection parts 12. Further, in the sensor unit 21, two kinesthetic-sense sensors 11D are provided on the substrate 22. As described above, the sensor unit 21 includes a plurality of kinesthetic-sense sensors whose heights from the substrate 22 to their contact parts 13 are different. By the above-described configuration, the modified example 4 of the embodiment can provide a five-fingered robot hand onto which a number of kinesthetic-sense sensors can be easily assembled.

As described above, according to the embodiment, the sensor system first selects, from signals acquired from a plurality of kinesthetic-sense sensors, calculation signals used for the calculation of a pressing force in the orthogonal-axis direction or a moment around the orthogonal axis, and then calculates the pressing force or the moment. In this way, it is possible to provide a sensor system capable of easily expanding its dynamic range while preventing or minimizing a decrease in the resolution with which an applied force is detected.

Note that the present disclosure is not limited to the above-described embodiments and they can be modified as desired without departing from the scope and spirit of the disclosure.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer through a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modified examples as would be obvious to one skilled in the art are intended for inclusion within the scope of the following claims.

What is claimed is:

1. A sensor system comprising:
   a substrate having a reference plane;
   a plurality of kinesthetic-sense sensors comprising first and second kinesthetic-sense sensors disposed on the substrate, each of the plurality of kinesthetic-sense sensors being configured to output signals of three axial directions corresponding to an orthogonal-axis direction orthogonal to the reference plane and two axial directions parallel to the reference plane, respectively, according to an external force from an object received at a force receiving part;
   a contact part tightly connected to the force receiving part and comprising a contact surface configured to come into contact with the object when the object is grasped; and
   a control unit configured to:
      determine whether or not a value of each of the signals of the three axial directions output by each of the plurality of kinesthetic-sense sensors is equal to or smaller than a predetermined threshold;
      select one or more signals among the signals output by the plurality of kinesthetic-sense sensors in response to determination that the value of each of the selected one or more signals of the three axial directions is equal to or smaller than the predetermined threshold; and
      calculate a pressing force in the orthogonal-axis direction or a moment around the orthogonal axis received from the object based on the selected one or more signals; and
   an output unit configured to output a result of the calculation,
   wherein a height from the contact surface of the contact part tightly connected to the force receiving part of the first kinesthetic-sense sensor to the reference plane is larger than a height from the contact surface of the contact part tightly connected to the force receiving part of the second kinesthetic-sense sensor to the reference plane.

2. The sensor system according to claim 1, wherein the plurality of kinesthetic-sense sensors are capacitance-type sensors.

3. The sensor system according to claim 1, wherein
   the substrate comprises a projection part including a top surface parallel to the reference plane, and
   the plurality of kinesthetic-sense sensors are disposed on the reference plane and the top surface, respectively.

4. The sensor system according to claim 3, wherein the projection part is compressible in the orthogonal-axis direction.

5. The sensor system according to claim 1, wherein the contact part is compressible in the orthogonal-axis direction.

6. The sensor system according to claim 1, wherein the control unit calculates the pressing force in the orthogonal-axis direction based on signals output by at least one of the plurality of kinesthetic-sense sensors that has output signals no larger than the threshold among the signals corresponding to the orthogonal-axis direction output by the plurality of kinesthetic-sense sensors.

7. A robot hand comprising:
   a plurality of grasping parts each comprising the substrate and the plurality of kinesthetic-sense sensors, the grasping parts being configured to grasp an object;
   a driving unit configured to move the plurality of grasping parts toward each other so that the grasping parts are opposed to each other; and
   a sensor system comprising:
      a substrate having a reference plane;
      a plurality of kinesthetic-sense sensors comprising first and second kinesthetic-sense sensors disposed on the substrate, each of the plurality of kinesthetic-sense sensors being configured to output signals of three axial directions corresponding to an orthogonal-axis direction orthogonal to the reference plane and two axial directions parallel to the reference plane, respectively, according to an external force from an object received at a force receiving part;
      a contact part tightly connected to the force receiving part and comprising a contact surface configured to come into contact with the object when the object is grasped; and
      a control unit configured to:
         determine whether or not a value of each of the signals of the three axial directions output by each of the plurality of kinesthetic-sense sensors is equal to or smaller than a predetermined threshold;

select one or more signals among the signals output by the plurality of kinesthetic-sense sensors in response to determination that the value of each of the selected one or more signals of the three axial directions is equal to or smaller than the predetermined threshold; and calculate a pressing force in the orthogonal-axis direction or a moment around the orthogonal axis received from the object based on the selected one or more signals; and an output unit configured to output a result of the calculation, wherein a height from the contact surface of the contact part tightly connected to the force receiving part of the first kinesthetic-sense sensor to the reference plane is larger than a height from the contact surface of the contact part tightly connected to the force receiving part of the second kinesthetic-sense sensor to the reference plane.

8. A method for calibrating a sensor system performed by a robot hand comprising:

a plurality of grasping parts each comprising the substrate and the plurality of kinesthetic-sense sensors, the grasping parts being configured to grasp an object;

a driving unit configured to move the plurality of grasping parts toward each other so that the grasping parts are opposed to each other; and a sensor system comprising:
  a substrate having a reference plane;
  a plurality of kinesthetic-sense sensors comprising first and second kinesthetic-sense sensors disposed on the substrate, each of the plurality of kinesthetic-sense sensors being configured to output signals of three axial directions corresponding to an orthogonal-axis direction orthogonal to the reference plane and two axial directions parallel to the reference plane, respectively, according to an external force from an object received at a force receiving part;
  a contact part tightly connected to the force receiving part and comprising a contact surface configured to come into contact with the object when the object is grasped; and
  a control unit configured to:
    determine whether or not a value of each of the signals of the three axial directions output by each of the plurality of kinesthetic-sense sensors is equal to or smaller than a predetermined threshold;
    select one or more signals among the signals output by the plurality of kinesthetic-sense sensors in response to determination that the value of each of the selected one or more signals of the three axial directions is equal to or smaller than the predetermined threshold; and
    calculate a pressing force in the orthogonal-axis direction or a moment around the orthogonal axis received from the object based on the selected one or more signals; and
  an output unit configured to output a result of the calculation,
  wherein a height from the contact surface of the contact part tightly connected to the force receiving part of the first kinesthetic-sense sensor to the reference plane is larger than a height from the contact surface of the contact part tightly connected to the force receiving part of the second kinesthetic-sense sensor to the reference plane, the method comprising:
grasping a reference object for calibration;
controlling a posture of the robot hand so that the reference plane becomes parallel or perpendicular to a gravitational direction;
determining whether or not calibration should be performed for the calculation result output by the sensor system in the controlled posture; and
setting a calibration value used for calibrating the output based on the determination.

9. A non-transitory computer readable medium storing a program for causing a computer to perform a method for calibrating a sensor system performed by a robot hand comprising:

a plurality of grasping parts each comprising the substrate and the plurality of kinesthetic-sense sensors, the grasping parts being configured to grasp an object;

a driving unit configured to move the plurality of grasping parts toward each other so that the grasping parts are opposed to each other; and a sensor system comprising:
  a substrate having a reference plane;
  a plurality of kinesthetic-sense sensors comprising first and second kinesthetic-sense sensors disposed on the substrate, each of the plurality of kinesthetic-sense sensors being configured to output signals of three axial directions corresponding to an orthogonal-axis direction orthogonal to the reference plane and two axial directions parallel to the reference plane, respectively, according to an external force from an object received at a force receiving part;
  a contact part tightly connected to the force receiving part and comprising a contact surface configured to come into contact with the object when the object is grasped; and
  a control unit configured to:
    determine whether or not a value of each of the signals of the three axial directions output by each of the plurality of kinesthetic-sense sensors is equal to or smaller than a predetermined threshold;
    select one or more signals among the signals output by the plurality of kinesthetic-sense sensors in response to determination that the value of each of the selected one or more signals of the three axial directions is equal to or smaller than the predetermined threshold; and
    calculate a pressing force in the orthogonal-axis direction or a moment around the orthogonal axis received from the object based on the selected one or more signals; and
  an output unit configured to output a result of the calculation,
  wherein a height from the contact surface of the contact part tightly connected to the force receiving part of the first kinesthetic-sense sensor to the reference plane is larger than a height from the contact surface of the contact part tightly connected to the force receiving part of the second kinesthetic-sense sensor to the reference plane, the method comprising:
grasping a reference object for calibration;
controlling a posture of the robot hand so that the reference plane becomes parallel or perpendicular to a gravitational direction;
determining whether or not calibration should be performed for the calculation result output by the sensor system in the controlled posture; and setting a calibration value used for calibrating the output based on the determination.

* * * * *